US006265421B1

(12) United States Patent
Pystynen et al.

(10) Patent No.: US 6,265,421 B1
(45) Date of Patent: Jul. 24, 2001

(54) PHOSPHOLAMBAN INHIBITORS AND A METHOD FOR INCREASING CORONARY FLOW

(75) Inventors: Jarmo Pystynen; Heimo Haikala, both of Espoo; Petri Kaheinen; Juha Kaivola, both of Helsinki; Piero Pollesello, Grankulla; Ismo Ulmanen, Vantaa; Jukka Tenhunen, Klaukkala; Carola Tilgmann, Jorvas; Eija Tiainen, Espoo; Kari Lönnberg, Routio; Pentti Nore, Helsinki; Seppo Parhi, Kiviniemi; Arto Karjalainen; Jouko Levijoki, both of Espoo, all of (FI)

(73) Assignee: Orion Corporation, Espoo (FI)

( * ) Notice: Subject to any disclaimer, the term of this patent is extended or adjusted under 35 U.S.C. 154(b) by 0 days.

(21) Appl. No.: 09/252,062

(22) Filed: Feb. 18, 1999

Related U.S. Application Data

(63) Continuation-in-part of application No. 09/159,776, filed on Sep. 24, 1998, now abandoned, and a continuation-in-part of application No. 08/937,118, filed on Sep. 24, 1997, now abandoned, which is a continuation-in-part of application No. 08/882,262, filed on Jun. 25, 1997, now abandoned, which is a continuation-in-part of application No. 09/104,114, filed on Jun. 25, 1998, now abandoned, which is a continuation-in-part of application No. 08/990,150, filed on Dec. 12, 1997, now abandoned, which is a continuation-in-part of application No. 08/937,119, filed on Sep. 24, 1997, now abandoned.

(51) Int. Cl.[7] .......................... A01N 43/40; A61K 31/445
(52) U.S. Cl. ............................................... 514/317; 546/79
(58) Field of Search ................................ 514/317; 546/79

(56) References Cited

U.S. PATENT DOCUMENTS

| 3,259,635 | 7/1966 | Ritter et al. ......................... 260/343.2 |
| 3,515,721 | * 6/1970 | Ritter et al. ......................... 260/247.2 |
| 4,349,566 | 9/1982 | della Valle ........................... 424/281 |
| 4,452,811 | 6/1984 | della Valle ........................... 424/281 |

OTHER PUBLICATIONS

Sutliff, R.L., et al., "Functional and Biochemical Evidence for Modulation of Endothelial Cell Function by Phospholamban," *FASEB J.* 12(5):A957 (Abstract No. 5546) (Mar. 1998).
STN Database CAPLUS, Document No. 94:15493, Joshi, B.S., et al., "Evaluation of some naturally occurring and synthetic coumarins for hypotensive activity," (1980).
STN Database CAPLUS, Document No. 77:88302, Murakami, M., et al., "Bis(carboxymethoxy)–4–methylcoumarins," (1972).
STN Database CAPLUS, Document No. 114:42491, Verma, B.S., et al., "Studies of pesticides based on coumarin: Part 5. Synthesis and antifungal activity of substituted 2,3–dihydrocyclopenta[c] [1] benzopyran–4(H)–ones," (1989).

STN Database CAPLUS, Document No. 97:216033, Winter, W., et al., "Tricyclic aryl ethers and medicines containing these compounds," (1982).
STN Database CAPLUS, Document No. 97:216005, Lesher, G.Y., and Philion, R.E., "3–Substituted–6–(lower alkyl)–5–(pyridinyl)–2(1H)–pyridinones, their cardiotonic use and intermediates therefor," (1982).
STN Database CAPLUS, Document No. 84:179971, Bartl, K., et al., "Synthesis of .DELTA.8–tetrahydrodibenzo[b,d]pyran–6–ones and their aminolysis to .DELTA.8–tetrahydrophenanthridine–6–ones," (1976).
STN Database CAPLUS, Document No. 84:179968, Chebaane, K., et al., "Synthesis of 2–arylnaphthalenes and of dibenzocoumarins. I. Synthesis of tetrahydrodibenzocoumarins, 2–(1–cyclohexenyl)naphthalenes and tetrahydrobenzocoumarins," (1975).
Ferguson, D.G., et al., "Localization of Phospholamban in Smooth Muscle Using Immunogold Electron Microscopy," *J. Cell Biol.* 107:555–562 (1988).
Ferrari, B., et al., "Development of Tetrazole Bioisosteres in Angiotensin II Antagonists," *Bioorg. & Med. Chem. Lett.* 4(1):45–50 (1994).
Gao, Y., et al., "Interaction of calmodulin with phospholamban and caldesmon: comparative studies by $^1$H–NMR spectroscopy," *Biochim. Biophys. Acta* 1160:22–34 (1992).
Hoh, J.F.Y., "Muscle fiber types and function," *Curr. Opin. Rheum.* 4:801–808 (1992).
Kohara, Y., et al., "Synthesis and Angiotensin II Receptor Antagonistic Activities of Benzimidazole Derivatives Bearing Acidic Heterocycles as Novel Tetrazole Bioisosteres," *J. Med. Chem.* 39:5228–5235 (Dec. 1996).
Lalli, J., et al., "Targeted Ablation of the Phospholamban Gene Is Associated With a Marked Decrease in Sensitivity in Aortic Smooth Muscle," *Circ. Res.* 80(4):506–513 (Apr. 1997).
Lindemann, J.P., et al., "β–Adrenergic Stimulation of Phospholamban Phosphorylation and $Ca^{2+}$–ATPase Activity in Guinea Pig Ventricles," *J. Biol. Chem.* 258(1):464–471 (1983).
Liu, L.H., et al., "Defective endothelium–dependent Relaxation of Vascular Smooth Muscle and Endothelial Cell $Ca^{2+}$ Signaling in Mice Lacking Sarco(endo)plasmic Reticulum $Ca^{2+}$–ATPase Isoform 3," *J. Biol. Chem.* 272(48):30538–30545 (Nov. 1997).
O'Neil, K.T., and DeGrado, W.F., "How calmodulin binds its targets: sequence independent recognition of amphiphilic α–helices," *Trends Biochem. Sci.* 15:59–64 (1990).

* cited by examiner

*Primary Examiner*—Dwayne C. Jones
(74) *Attorney, Agent, or Firm*—Sterne, Kessler, Goldstein & Fox P.L.L.C.

(57) ABSTRACT

A method for obtaining direct dilatation of the coronary arteries by administering a therapeutically effective amount of a phospholamban inhibitor is described. Compounds which are effective in relieving the inhibitory effects of phospholamban on cardiac sarcoplasmic reticulum $Ca^{2+}$-ATPase are also described.

33 Claims, 6 Drawing Sheets

PHOSPHOLAMBAN INHIBITORS AND A METHOD FOR INCREASING CORONARY FLOW

CROSS-REFERENCE TO RELATED APPLICATIONS

This is a continuation-in-part of U.S. application Ser. No.08/937,118, filed on Sep. 24, 1997, abandoned on Feb. 24, 1999, and of U.S. application Ser. No.09/159,776, filed on Sep. 24, 1998, abandoned on Dec. 15, 1998; said U.S. application Ser. No. 08/937,118 is a continuation-in-part of U.S. application Ser. No. 08/882,262, filed on Jun. 25, 1997, abandoned on Feb. 6, 1998; said U.S. application Ser. No. 09/159,776 is a continuation-in-part of U.S. application Ser. No. 09/104,114, filed on Jun. 25, 1998, now abandoned, which is a continuation-in-part of U.S. application Ser. No. 08/990,150, filed on Dec. 12, 1997, abandoned on Oct. 3, 1998, which is a continuation-in-part of U.S. application Ser. No.08/937,119, filed on Sep. 24, 1997, abandoned on Oct. 3, 1998. The entirety of each of these applications is incorporated by reference herein.

BACKGROUND OF THE INVENTION

This invention relates to a method for increasing coronary flow. Particularly, the invention relates to a method for obtaining direct dilatation of the coronary arteries by administering a phospholamban inhibitor as the active compound. The present invention also relates to novel phospholamban inhibitors, pharmaceutical compositions containing these compounds and new intermediates. Novel phospholamban inhibitors are also useful in the treatment of heart failure and stunned myocardium.

Contraction of the muscle cell is controlled by the amount of free cytosolic calcium interacting with calmodulin in smooth muscle cells or with troponin C in cardiac and skeletal muscle cells. These calcium-activated proteins trigger a cascade of events leading to cell shortening and muscle contraction.

One of the most important enzymes which aids to terminate or prevent the muscle contraction is the Ca2+-ATPase located inside the cell in the sarcoplasmic reticulum (SR). This enzyme transfers cytosolic calcium against the concentration gradient into the intracellular calcium storages. The function of the SR $Ca^{2+}$-ATPase (SERCA) is controlled by a small protein called phospholamban. When phospholamban is unphosphorylated, it inhibits the SERCA. In contrast, when phosphorylated, phospholamban does not inhibit this calcium pump. The removal of the inhibitory effect of phospholamban is seen as a stimulation of the calcium uptake into the SR, since some of the SERCA molecules are all the time under the inhibitory control of phospholamban.

Phospholamban has been shown to have an important role in the cardiac muscle (Lindemann, J. P. et al., "Beta-adrenergic stimulation of phospholamban phosphorylation and $Ca^{2+}$-ATPase activity in guinea pig ventricles", J. Biol. Chem. 258:464–471, 1983) and in the slow skeletal muscles, whereas the fast skeletal muscle does not express phospholamban at all (Hoh, J. F. Y, "Muscle fiber types and function", Current Opinion in Rheumatology, 4:801–808, 1992). Moreover, phospholamban is expressed in mouse aorta (Lalli, J. et al., "Targeted ablation of the phospholamban gene is associated with a marked decrease in sensitivity in aortic smooth muscle", Circ. Res. 80(4): 506–513, 1997) and thereby it is thought that phospholamban controls SERCA in peripheral vascular tissue.

Through its inhibitory effects on the SERCA present in the cardiac tissue phospholamban represses both the rates of relaxation and contraction in the mammalian heart. Therefore, a compound capable of relieving the inhibitory effects of phospholamban on cardiac SERCA, e.g. by interrupting phospholamban-SERCA interaction, would be useful in the treatment of heart failure.

Evidence was very recently given that PLB is present in aortic endothelial cells (Sutliff, R. L. et al., "Functional and biochemical evidence for modulation of endothelial cell function by phospholamban", FASEB Journal 12 (5):A957, 1998), where it modulates the activity of the isoform of SERCA present on the endoplasmic reticulum. It was also shown that a decreased activity of the endoplasmic reticulum calcium pumping in aortic endothelial cells is leading to defective endothelium-dependent relaxation of aortic vascular smooth muscle (Liu, L. H. et al., "Defective endothelium-dependent relaxation of vascular smooth muscle and endothelial cell $Ca^{2+}$ signalling in mice lacking sarco(endo)plasmic reticulum $CA^{2+}$-ATPase isoform 3", J. Biol. Chem. 272(48):30538–30545, 1997).

There is no published evidence of the presence of phospholamban in the endothelial cells of coronary arteries.

SUMMARY OF THE INVENTION

It has now been found that compounds of formulae (I) or (II) are effective in relieving the inhibitory effects of phospholamban on cardiac SR $Ca^{2+}$-ATPase (SERCA). The compounds of formulae (I) or (II) act as phospholamban inhibitors through direct binding to the phospholamban protein. Thereby, compounds of formulae (I) or (II) eliminate the inhibitory action of phospholamban on the SERCA like the protein kinases as they phosphorylate phospholamban.

Furthermore, it was surprisingly found that the phospholamban inhibitors of formula (I) or (II) increased coronary flow in isolated paced guinea-pig heart perfused with constant pressure. The magnitude of the effect on coronary flow markedly exceeded the increasing effects of the compounds on the relaxation and contraction velocities of the left ventricle of the heart indicating that compounds of formula (I) or (II) directly dilate the coronary arteries. The effect of compounds (I) or (II) on coronary flow preceded the other effects confirming that the coronary dilatation was due to the direct effect of the compounds on the coronary arteries. Furthermore, it was found that the vasodilatory effect of the phospholamban inhibitors of (I) or (II) is due to an endothelial-mediated mechanism. Therefore, we propose that phospholamban inhibitors induce vasodilatation and enhance the coronary flow by blocking the inhibitory effect of PLB on SERCA on the endoplasmic reticulum of the endothelial cells of the coronary arteries.

Having the unexpected ability to directly dilatate the coronary arteries, phospholamban inhibitors, such as compounds (I) or (II), are useful in the treatment of conditions where an increase in the coronary flow is desired, e.g. in coronary heart disease and in hemodynamic crisis in which the low aortic blood pressure decreases coronary perfusion pressure.

Compounds of the present invention have the structure represented by formulae (I) or (II):

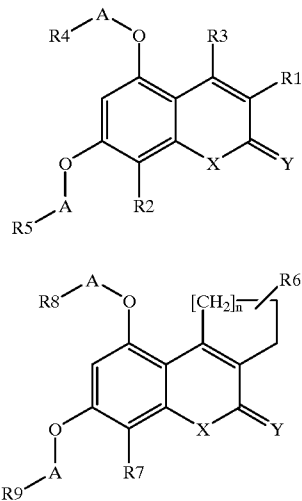

(I)

(II)

in which

R₁ is hydrogen, alkyl, alkenyl, aryl, arylalkyl, hydroxyalkyl, halogenalkyl, alkoxy, $COR_{10}$, $CONR_{10}R_{11}$, $OR_{10}$, $S(O)_mR_{10}$, $NR_{10}COR_{11}$ or $NR_{10}R_{11}$, where $R_{10}$ is hydrogen, alkyl, alkenyl, aryl, arylalkyl, hydroxyalkyl, halogenalkyl, alkoxy or hydroxy and $R_{11}$ is hydrogen, alkyl, aryl, arylalkyl, alkoxy, aryloxy, hydroxy or acyl, or in case where X is $NR_{11}$, can $R_1$ also be carboxylalkyl, R₆ is hydrogen, alkyl, alkenyl, aryl, arylalkyl, R₂ and R₇ mean hydrogen, alkyl, aryl, arylalkyl, alkenyl, $COR_{10}$, $CONR_{10}R_{11}$, halogen, trifluoromethyl, nitro or cyano, where $R_{10}$ and $R_{11}$ are defined as above, R3 is hydrogen, alkyl, aryl or arylalkyl, A means alkyl or substituted alkyl, m is 0–2 and n is 1–3, Y means O, NR11 or S, where R11 is the same as above, X means O, NR11 or S, where R11 is the same as above, R₄, R₅, R₈ and R₉ mean independently one of the following groups:

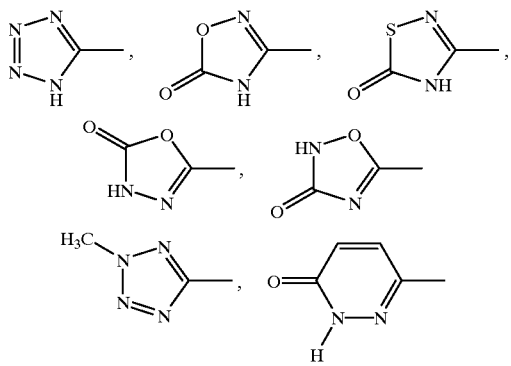

or in case where X is $NR_{11}$, can $R_4$, $R_5$, $R_8$ and $R_9$ also independently mean HOOC—, $R_{12}$OOC—, $H_2NCO$— or HOHNCO— wherein $R_{12}$ means alkyl, arylalkyl or aryl, and wherein each aryl residue defined above by itself or as part of another group may be substituted, and pharmaceutically acceptable salts and esters thereof.

In one class of preferred compounds and pharmaceutically acceptable salts and esters thereof are compounds of formula (I) wherein R2 is hydrogen. In a subclass of this class of compounds and pharmaceutically acceptable salts and esters thereof R1 is hydrogen, $C_{1-6}$ alkyl, $C_{2-6}$ alkenyl, $C_{6-10}$ aryl, $C_{7-12}$ arylalkyl, $C_{1-6}$ hydroxyalkyl, $C_{1-6}$ halogenalkyl or $C_{1-6}$ alkoxy. In a group of this subclass of compounds and pharmaceutically acceptable salts and esters thereof, Y is O or S, preferably O; and X is O. In another group of this subclass of compounds and pharmaceutically acceptable salts and esters thereof, Y is O or S, preferably O; and X is NR11, where R11 is hydrogen, $C_{1-6}$ alkyl, $C_{6-10}$ aryl, $C_{7-12}$ arylalkyl, $C_{1-6}$ alkoxy, $C_{6-10}$ aryloxy, hydroxy, $C_{1-6}$ alkanoyl or $C_{1-6}$ carboxyalkyl. In a subgroup of these group of compounds and pharmaceutically acceptable salts and esters thereof, R3 is hydrogen, $C_{1-6}$ alkyl, $C_{6-10}$ aryl, or $C_{7-12}$ arylalkyl, preferably $C_{1-6}$ alkyl, most preferably methyl. In a family of these subgroups of compounds and pharmaceutically acceptable salts and esters thereof, A is preferably straight-chain or branched $C_{1-4}$ alkylene.

In another preferred class of compounds and pharmaceutically acceptable salts and esters thereof, compounds have formula (II) wherein R7 is hydrogen. In a subclass of this class of compounds and pharmaceutically acceptable salts and esters thereof R6 is hydrogen, $C_{1-6}$ alkyl, $C_{6-10}$ aryl, $C_{7-12}$ arylalkyl; and n is 1, 2 or 3, preferably 1 or 2. In a group of this subclass of compounds and pharmaceutically acceptable salts and esters thereof, Y is O or S, preferably O; and X is O. In another group of this subclass of compounds and pharmaceutically acceptable salts and esters thereof, Y is O or S, preferably O; and X is NR11, where R11 is hydrogen, $C_{1-6}$ alkyl, $C_{6-10}$ aryl, $C_{7-12}$ arylalkyl, $C_{1-6}$ alkoxy, $C_{6-10}$ aryloxy, hydroxy, $C_{1-6}$ alkanoyl or $C_{1-6}$ carboxyalkyl. In a subgroup of these group of compounds and pharmaceutically acceptable salts and esters thereof, A is preferably straight-chain or branched $C_{1-4}$ alkylene.

Each aryl residue in each of these preferred classes of compounds, by itself or as part of another group, may be substituted by 1 to 3, preferably 1 or 2, most preferably one of fluorine, chlorine, bromine, iodine, trifluoromethyl, amino, $C_{1-4}$ alkyl, $C_{1-4}$ alkoxy, phenyl, naphthyl, halophenyl, halonaphthyl, benzyl, phenethyl, halobenzyl, halophenethyl, naphthylmethyl, naphthylethyl, $C_{4-7}$ cycloalkyl, $C_{1-4}$ alkyl ($C_{4-7}$)cycloalkyl, hydroxy, mono-($C_{1-4}$)alkylamino, di-($C_{1-4}$)alkylamino, $C_{1-6}$ alkanoylamino, phenylcarbonylamino, naphthylcarbonylamino nitro, cyano, thiol, or $C_{1-6}$ alkylthio.

DETAILED DESCRIPTION OF THE INVENTION

Figure 1:
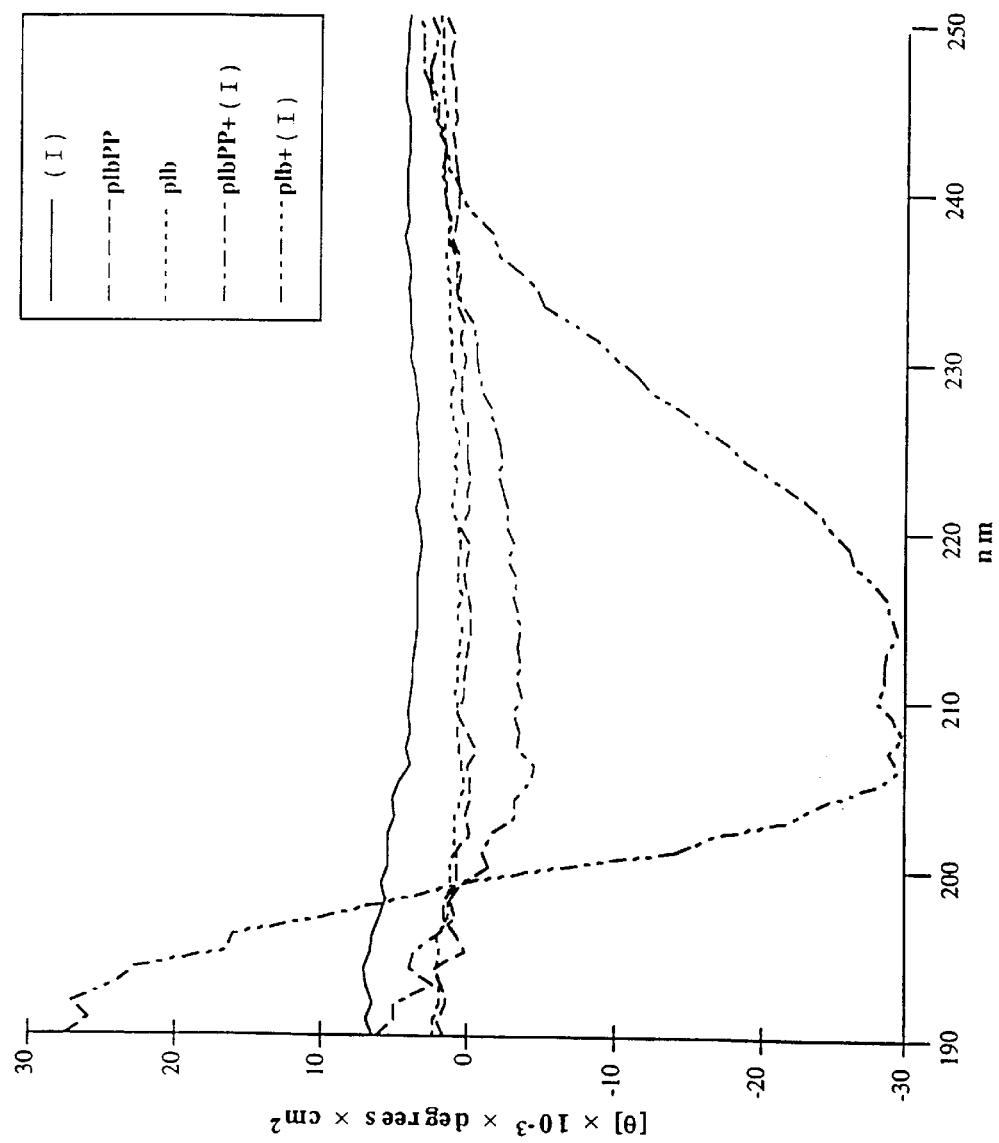
FIG. 1 shows CD spectra of 50 μM of PLB[1–36 a.a] (plb), PLB[1–36 a.a.](Ser16PO₃-, Thr17PO₃-) (plbPP), compound of Example 1c, and of the mixtures PLB[1–36 a.a]+compound of Example 1c and PLB[1–36 a.a.] (Ser16PO₃-, Thr17PO₃-)+compound of Example 1c in water at room temperature.

The present invention provides a method for obtaining direct dilatation of the coronary arteries comprising administering to a mammal in need thereof a therapeutically effective amount of a phospholamban inhibitor as the active compound. Furthermore, the invention provides a method for the treatment of coronary heart disease comprising administering to a mammal in need thereof a therapeutically effective amount of a phospholamban inhibitor. The invention also provides method for the treatment of hemodynamic crisis in which the low aortic blood pressure decreases coronary perfusion pressure comprising administering to a mammal in need thereof a therapeutically effective amount of a phospholamban inhibitor.

The term "phospholamban inhibitor" means here a compound which relieves the inhibitory effect of phospholamban on SR $Ca^{2+}$-ATPase by direct binding to the phospholamban protein.

The inhibitory effect of a given compound on phospholamban can be demonstrated by measuring the effect of the compound on calcium uptake into the SR vesicles prepared from cardiac tissue and into SR vesicles prepared from fast skeletal muscle (psoas m.). Both kind of SR vesicles contain $Ca^{2+}$-ATPase but the vesicles from the fast skeletal muscle do not contain phospholamban (Hoh JFY, "Muscle fiber types and function", Current Opinion in Rheumatology, 4:801–808, 1992). An increase in the calcium uptake into the SR vesicles prepared from cardiac tissue but not into the SR vesicles prepared from fast skeletal muscle indicates that the compound relieves the inhibitory effect of phospholamban on SR $Ca^{2+}$-ATPase by direct binding to the phospholamban protein and that the compound is applicable as a phospholamban inhibitor in the method of the invention. The direct binding of a compound to the phospholamban protein can be ascertained by the circular dichroism (CD) spectroscopy. The methods for determining whether a compound relieves the inhibitory effect of phospholamban on SR $Ca^{2+}$-ATPase by direct binding to the phospholamban protein, i.e. is a phospholamban inhibitor, are illustrated in detail in the experimental section.

The compounds of formula (I) or (II) can be prepared from the 1,3-dihydroxy substituted heteroaromatics by alkylation of the dihydroxy compounds by suitable alkylating agents, for example by chloroacetonitrile or bromoacetic ester according to the following Scheme 1, wherein $R_1, R_2, R_3$, X and Y are the same as defined above, R' is a protecting group for the hydroxyl, e.g. methyl, benzyl or tetrahydropyranyl.

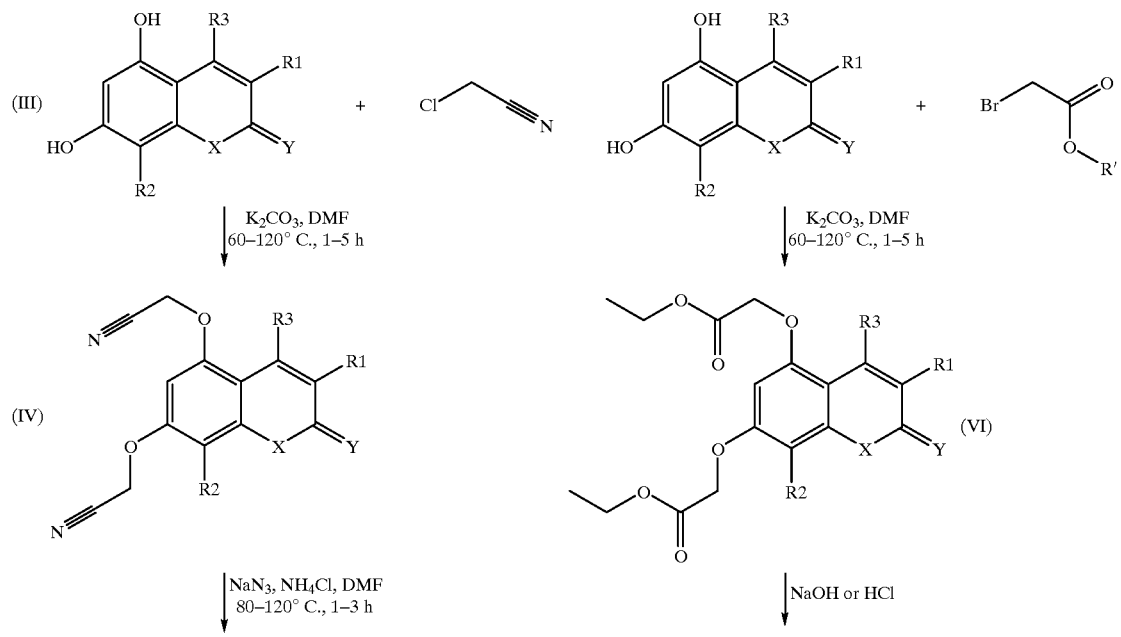

SCHEME 1

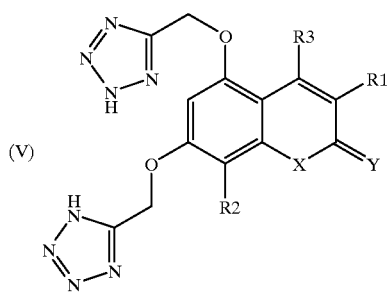

(V)

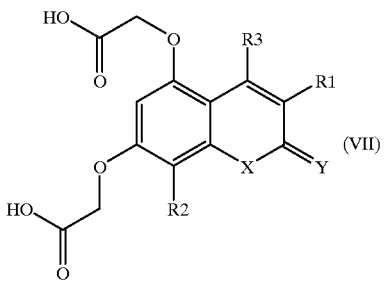

(VII)

The cyano compound (IV) described above is used to prepare the 1,2,4-oxadiazole and 1,2,4-thiadiazole derivatives using the methods described in J. Med. Chem. 1996, 39, 5228–5235.

The syntheses are shown in Scheme 2, wherein $R_1$, $R_2$, $R_3$, X and Y are the same as defined above.

The dihydroxyaromatics (III) are made by use of the literature methods. The coumarins (XIV), (XVI) and (XX) are made by the use of the Knoevenagel condensation or von Pechmann reaction as presented in Scheme 3 and 4, where

SCHEME 2

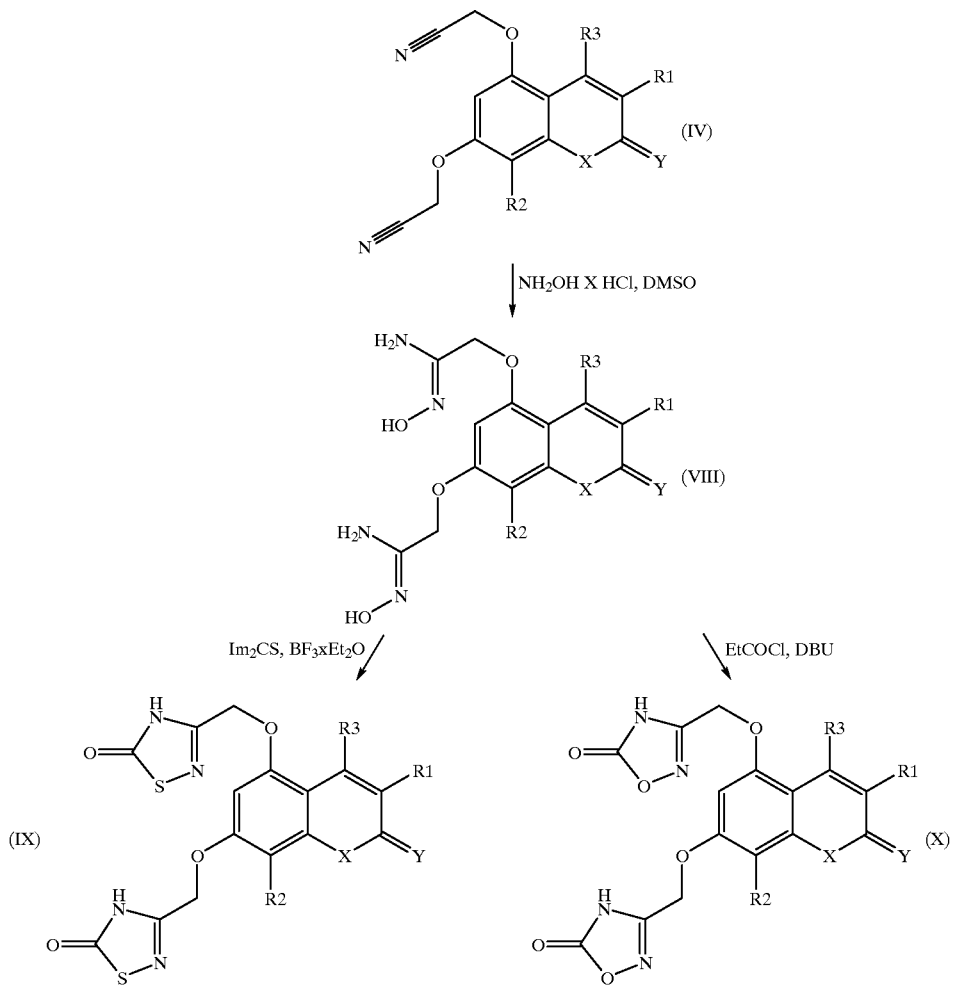

The other heterocyclics as groups $R_4$, $R_5$, $R_8$ and $R_9$ are prepared as described in Bioorg. Med. Chem. Lett., 1994, 4, 45–50.

$R_1$, $R_2$ and $R_3$, are the same as defined above, Z is alkyl, aryl, arylalkyl or alkenyl and R' is a protecting group for the hydroxyls e.g. methyl, benzyl or tetrahydropyranyl.

SCHEME 3
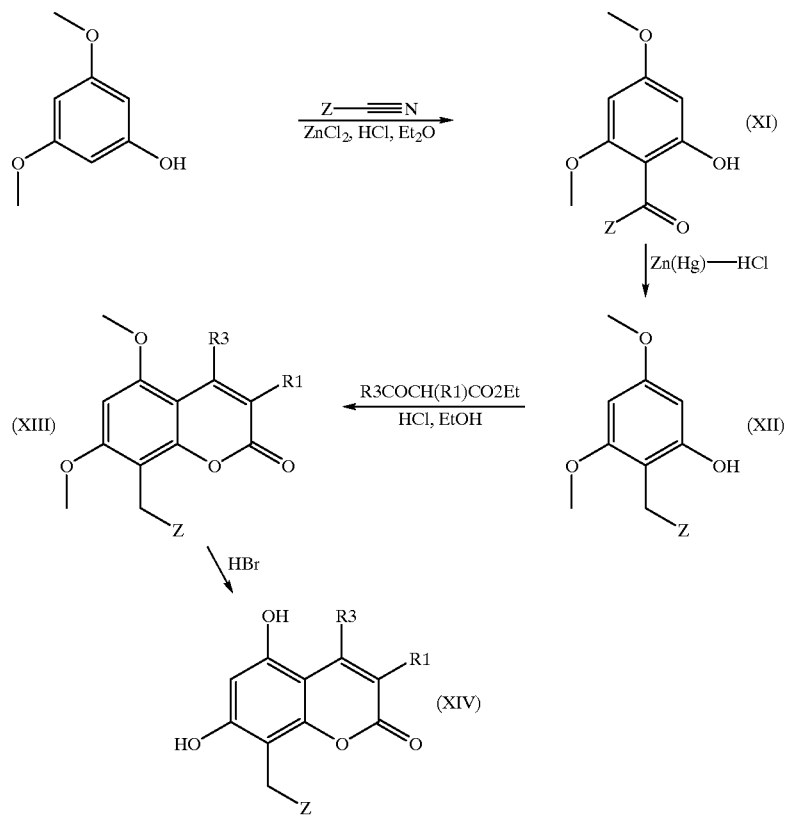
SCHEME 4
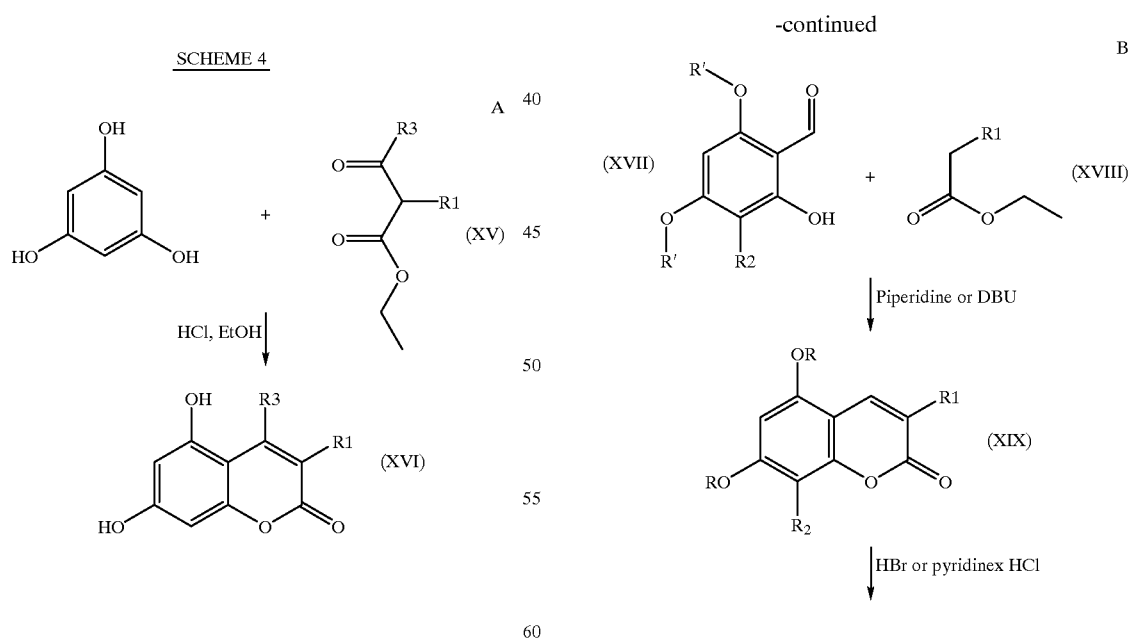

-continued

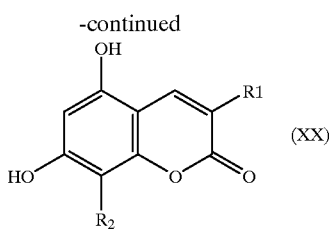
(XX)

The quinolinones are prepared by the Knorr reaction as described in Scheme 5, wherein $R_1, R_{11}$ and $R_3$ are the same as defined above, X is a halogen.

SCHEME 5

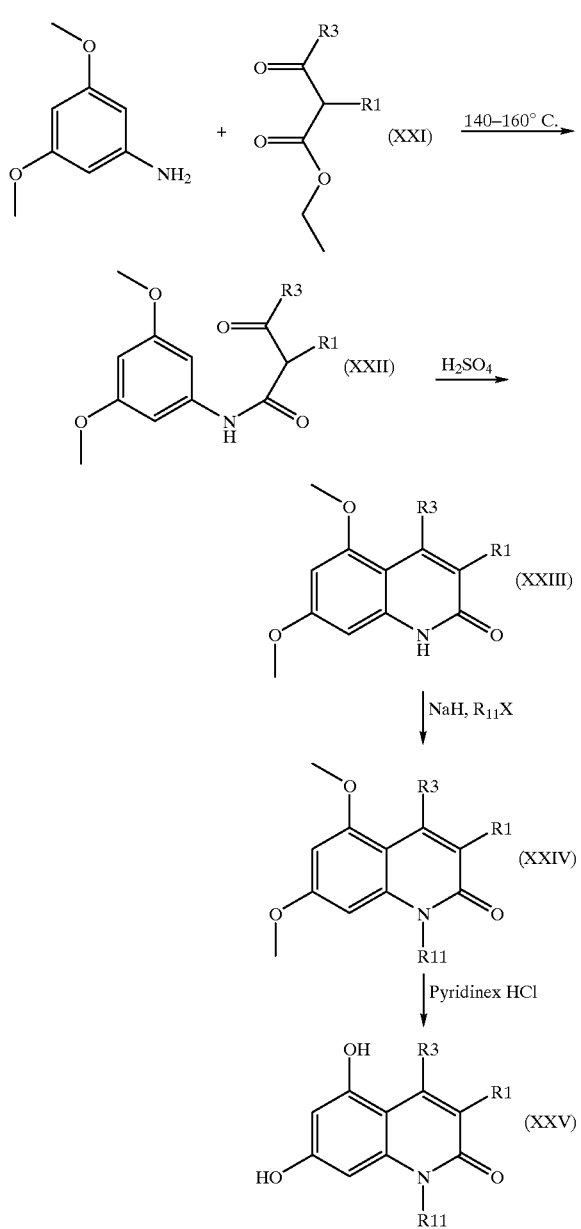

The cyclic compounds (II) can be prepared correspondingly from compound (XXXI) which can be prepared according to the Scheme 6, wherein $R_2$ and $R_6$ are the same as defined above, R' is a protecting group for the hydroxyls e.g. methyl, benzyl or tetrahydropyranyl.

SCHEME 6

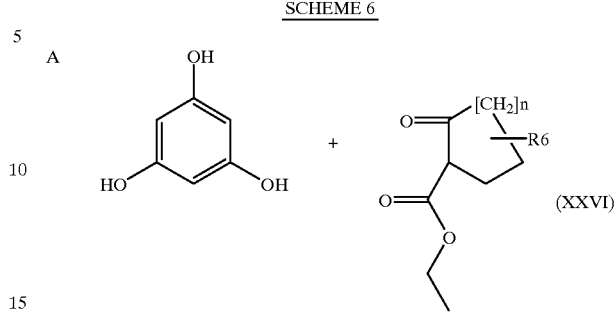

Cyclic quinolinone compounds (II) can be prepared correspondingly from (XXVI) using Scheme 5.

Salts and esters of the compounds, when applicable, may be prepared by known methods. Physiologically acceptable salts are useful as active medicaments, however, preferred are the salts with alkali or alkaline earth metals. Physiologically acceptable esters are also useful as active medicaments. Examples are the esters with aliphatic or aromatic alcohols.

The term "alkyl" as employed herein by itself or as part of another group includes both straight, branched and cyclized chain radicals of up to 18 carbon atoms, preferably 1 to 8 carbon atoms, most preferably 1 to 4 carbon atoms. The term "lower alkyl" as employed herein by itself or as part of another group includes straight, branched and cyclized chain radicals of 1 to 7, preferably 1 to 4, most preferably 1 or 2 carbon atoms. Specific examples for the alkyl and lower alkyl residues, respectively, are methyl, ethyl, propyl, isopropyl, butyl, tert. butyl, pentyl, cyclopentyl, hexyl, cyclohexyl, octyl, decyl and dodecyl including the various branched chain isomers thereof.

The term "acyl" as employed herein by itself or as part of another group refers to an alkylcarbonyl or alkenylcarbonyl group, the alkyl and alkenyl groups being defined above.

The term "aryl" as used herein by itself or as part of another group refers to a monocyclic or bicyclic group containing from 6 to 10 carbon atoms in the ring portion. Specific examples for aryl groups are phenyl, naphtyl and the like. "Aroyl" means in a corresponding way an arylcarbonyl group.

The term "alkoxy" as employed herein by itself or as part of another group includes an alkyl group as defined above linked to an oxygen atom. "Aryloxy" means in a corresponding way an aryl group linked to an oxygen atom.

The term "substituted" as used herein in connection with various residues refers to halogen substituents, such as fluorine, chlorine, bromine, iodine or trifluoromethyl group, amino, alkyl, alkoxy, aryl, alkyl-aryl, halogen-aryl, cycloalkyl, alkylcycloalkyl, hydroxy, alkylamino, alkanoylamino, arylcarbonylamino, nitro, cyano, thiol, or alkylthio substituents.

The term "substituted" as used herein in connection with various residues refers to halogen substituents, such as fluorine, chlorine, bromine, iodine or trifluoromethyl group, amino, alkyl, alkoxy, aryl, alkyl-aryl, halogen-aryl, cycloalkyl, alkylcycloalkyl, hydroxy, alkylamino, alkanoylamino, arylcarbonylamino, nitro, cyano, thiol, or alkylthio substituents.

The "substituted" groups may contain 1 to 3, preferably 1 or 2, most preferably 1 of the above mentioned substituents.

Phospholamban inhibitors such as compounds of formula (I) or (II) may be administered to a patient in therapeutically effective amounts which range usually from about 0.1 to 500 mg, more usually from about 0.5 to 50 mg, per day depending on the age, weight, condition of the patient, administration route and the phospholamban inhibitor used. The term "therapeutically effective amount" means here an amount which produces a direct dilatation of the coronary arteries of a patient. The active compound of the invention, which can be compound of formula (I) or (II) or any compound possessing phospholamban inhibiting activity as defined above, can be formulated into dosage forms using the principles known in the art. It can be given to a patient as such or in combination with suitable pharmaceutical excipients in the form of tablets, dragees, capsules, suppositories, emulsions, suspensions or solutions. Choosing suitable ingredients for the composition is a routine for those of ordinary skill in the art. It is evident that suitable carriers, solvents, gel forming ingredients, dispersion forming ingredients, antioxidants, colours, sweeteners, wetting compounds and other ingredients normally used in this field of technology may be also used. The compositions containing the active compound can be given enterally or parenterally, the oral route being the preferred way. The contents of the active compound in the composition is from about 0.5 to 100%, preferably from about 0.5 to about 20%, per weight of the total composition.

Experiments

The effect of the compounds of the invention on phospholamban was verified by measuring its effects on calcium uptake into the SR vesicles prepared from cardiac tissue and into vesicles prepared from fast skeletal muscle (psoas m.). Both kind of SR vesicles contain $Ca^{2+}$-ATPase but the vesicles from the fast skeletal muscle do not contain phospholamban (Hoh JFY, "Muscle fiber types and function", Current Opinion in Rheumatology, 4:801–808, 1992). These calcium uptake experiments showed that compound of Example 1c was active only in vesicles prepared from cardiac tissue suggesting that the effect was based on the relief of phospholamban inhibition. In addition to this, the direct binding of the compound of Example 1c to phospholamban was demonstrated by using circular dichroism spectroscopy. Furthermore, the expression of phospholamban in porcine coronary arteries was proved by mRNA measurements and by using specific antibodies against phospholamban. Furthermore, the effects of compound of Example 1c on the coronary flow and on the left ventricular pressure derivatives in isolated paced guinea-pig heart perfused with constant pressure are demonstrated. Furthermore, the endothelial-mediated mechanism of the vasodilatory effect of the compounds of the invention is demonstrated. Finally, the effect of the compounds of the invention on the development of stunned myocardium is demonstrated. The methods are described below in detail.

Experiment 1. Effects on calcium uptake into the SR vesicles prepared from cardiac and fast skeletal muscle Preparation of the SR-vesicles Guinea pigs (10–12) were decapitated. Their hearts or the psoas muscles were excised, washed in ice-cold 0.9% NaCl and cut into pieces in a buffer containing 20 mM Tris-maleate, 0.3 M sucrose, pH 7.0. Thereafter tissue pieces were homogenized with Polytron and further with Potter (10 strokes). The homogenate was centrifugated at 1000 g for 15 min at 4° C. The supernatant was collected and the pellet was resuspended into 5 ml of the buffer (20 mM Tris-maleate, 0.3 M sucrose, pH 7.0) and recentrifugated at 1000 g for 10 min at 4° C. The obtained supernatant was combined with the earlier collected supernatant and centrifugated once again at 10 000 g for 20 min at 4° C. The final supernatant was filtered into a bottle equipped with a magnetic stirrer. KCl was added to the filtered supernatant to achieve the final concentration of 0.6 M (at 4° C.). The obtained solution was centrifugated at 100 000 g for 60 min at 4° C. The pellet was suspended in 5 ml of the buffer containing 20 mM Tris-maleate, 0.3 M sucrose, pH 7.0 and centrifugated at 100 000 g for 60 min at 4° C. The obtained pellet was suspended in 5 ml of buffer containing 20 mM Tris-maleate, 0.3 M sucrose, 0.1 M KCl, pH 7.0 and stored at −80° C. until use. The protein concentration was also measured in order to standardise the separately prepared vesicle preparations.

Calcium uptake assay

In the calcium uptake assay, the fluorescent indicator, fluo-3 was used to detect the decrease of the extravesicular $Ca^{2+}$-concentration, when the SR $Ca^{2+}$ATPase was transferring $Ca^{2+}$ from the extravesicular space into the SR-vesicles.

The SR-vesicles obtained above (50 μg protein/ml) were pre-incubated with or without the test compound at 37° C. for 5 min in the assay buffer containing 40 mM imidazole, 95 mM KCl, 5 mM $NaN_3$, 5 mM $MgCl_2$, 0.5 mM EGTA, 5 mM potassium oxalate, 2 μM ruthenium red, 5 μM fluo-3, pH 7.0. The free calcium was adjusted to 0.1 μM or to 0.04 μM by $CaCl_2$. The reaction was initiated by adding ATP (5 mM). The final reaction volume was 1.5 ml. The fluorescence of reaction mixture was measured for 3 min by using the excitation and emission wavelengths of 510 nm and 530 nm, respectively.

Results

Figure 2A:
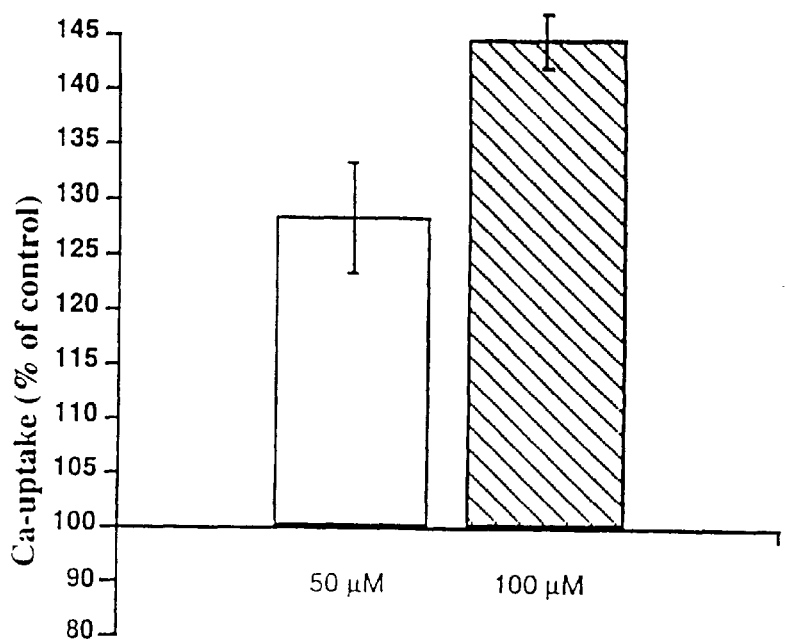
FIG. 2A shows the effect of compound of Example 1c (50 and 100 μM) on the Ca²⁺ uptake rate into the cardiac muscle SR vesicles.
Figure 2B:
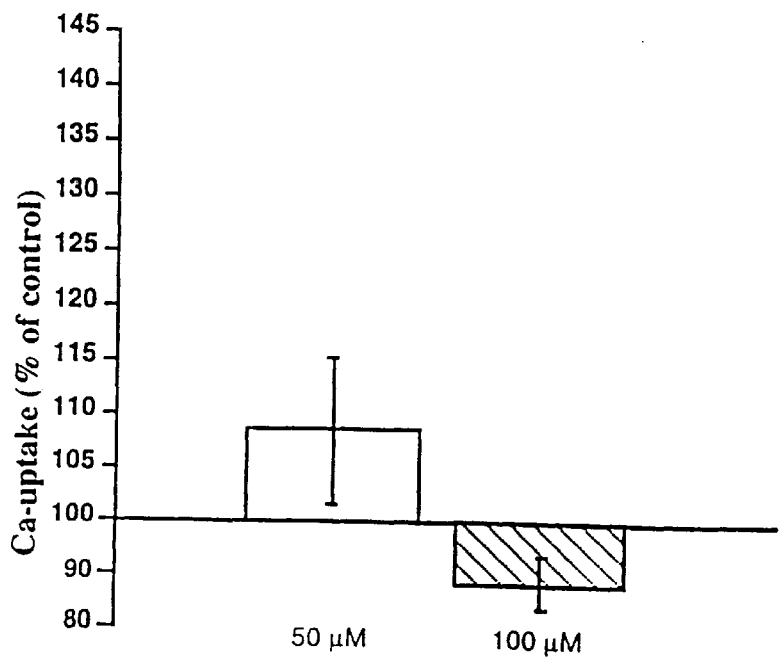
FIG. 2B shows the effect of compound of Example 1c (50 and 100 μM) on the Ca²⁺ uptake rate into the fast skeletal muscle SR vesicles.

FIGS. 2A and 2B show the effect of compound of Example 1c (50 and 100 $\mu$M) on the $Ca^{2+}$ uptake rate into the cardiac (A) and fast skeletal muscle (B) SR vesicles. Given are means ±SEM from three experiments per group. It can be seen that compound of Example 1c accelerated the calcium uptake into the cardiac SR vesicles but did not change the calcium uptake into the SR vesicle prepared from the fast skeletal muscle.

Table 1 shows the effects of various other phospholamban inhibitors of formula (I) or (II) on the $Ca^{2+}$ uptake rate into the cardiac (A) and fast skeletal muscle (B) SR vesicles. The experiments were carried out at 0.1 $\mu$M and 0.04 $\mu$M free calcium concentrations, respectively.

TABLE 1

Stimulation (%) of the $Ca^{2+}$ uptake into the vesicle preparations obtained from the ventricular myocardium (A) and fast skeletal muscle (B) of the guinea-pig heart.

| Compound of | The stimulation (%) of $Ca^{2+}$ uptake | |
|---|---|---|
| Example No. | A | B |
| 3c*** | 51 | 0 |
| 2c* | 26 | −1 |
| 7c* | 5 | −17 |
| 8g**** | 18 | 0 |
| 11b* | 28 | nd |
| 12* | 32 | nd |
| 13d** | 23 | nd |
| 14c**** | 18 | nd |
| 18e* | 13 | nd |
| 21* | 11 | nd |
| 23***** | 20 | nd |

***5 $\mu$M, 10 $\mu$M, *20 $\mu$M, **50 $\mu$M, *100 $\mu$M
nd = not determined Experiment 2. Binding of compound of Example 1c to the cytosolic part of phospholamban demonstrated by circular dichroism (CD) spectroscopy Both the 36 amino acid N-terminal fragment of human phospholamban (PLB [1–36 a.a.]) and the 36 amino acid N-terminal fragment of double phosphorylated human phospholamban (PLB [1–36 a.a.](Ser16PO$_3$-, Thr17PO$_3$-)) were obtained by peptide synthesis. The peptides were purified by reverse phase HPLC, analysed for homogenity by mass spectrometry and were found pure at 97%. The peptides were lyophilized and then resuspended in water at the final concentration of 0.1 mM, for CD analysis. The pH of both solutions was between 3 and 4 and was not further adjusted. Compound of Example 1c was solved in water at a final concentration of 0.1 mM. The pH was adjusted at 7.2 by adding 1 N NaOH.

Circular dichroism spectra were acquired at 24° C. on samples of 100 $\mu$l. The spectra were recorded on a Jasco J-720 spectropolarimeter using a 1 mm path-length quartz cuvette. The band width was 1 nm, the sensitivity 20 mdeg, the step resolution 0.5 nm, the response time 0.5 sec, and the scan speed 20 nm/min (from 250 to 190 nm). The spectra were expressed in $[\theta] \times 10^{-3} \times degrees \times cm^2 \times dmol^{-1}$.

The CD spectra of PLB[1–36 a.a] and of the mixtures PLB[1–36 a.a]+compound of Example 1c show that a dramatic change in the average structure of the peptide takes place after addition of compound of Example 1c. A marked increase of $\alpha$-helical contribution can be seen (FIG. 1). Such a behaviour was shown for many Calmodulin-binding peptides, which form helices in the bound state. CD studies showed that when such peptides bind Calmodulin, there is an increase in helicity of the complex over the sum of the two individual non interacting components (for a review, see: O'Neil, K. T. and DeGrado, W. F. "How calmodulin binds its targets: sequence independent recognition of amphiphilic $\alpha$-helices", TIBS 15:59–64, 1990). Moreover, it was previously demonstrated by NMR that the N-terminal fragment of PLB [aa.1–25] interacts directly with Calmodulin (Gao, Y. et al. "Interaction of calmodulin with phospholamban and caldesmon: comparative studies by $^1$H-NMR spectroscopy", Biochim. Biophys. Acta 1160: 22–34, 1992). The present experiment thus verifies that compound of Example 1c forms a complex with PLB at his N-terminal domain.

Compound of Example 1c, added to PLB[1–36 a.a.] (Ser16PO$_3$-, Thr17PO$_3$-), is not influencing the structure of the phosphorylated peptide as much as for the unphosphorylated. The CD measurements show that compound of Example 1c interacts with the cytosolic part of phospholamban PLB[1–36 a.a.], and does not interact or interacts weakly with the phosphorylated phospholamban (PLB[1–36 a.a.](Ser16PO$_3$-, Thr17PO$_3$-)). Thus, the interaction is specific for the unphosphorylated phospholamban.

Experiment 3. Detection of phospholamban and $Ca^{2+}$-ATPase polypeptides by immunoblotting from porcine heart tissue Methods Tissue samples of the left ventricular myocardium of the heart, aorta, the proximal coronary artery (the first 2 cm of the coronary artery starting from the aorta) as well as of the more distal coronary artery (the next 2 cm) obtained and pooled from three pigs were powdered under liquid nitrogen and the powders suspended in homogenization buffer (50 mM K$^+$-phosphate-buffer pH 7.0, 10 mM NaF, 1 mM EDTA, 0.3 mM PMSF, 0.5 mM DTT, 0.3 M sucrose). Each tissue sample was homogenized at (1100 rpm) with a Potter-Elvehjelm homogenizer at +4° C. 20 times. The protein concentration was measured according to Bradford, M., (1976), Anal. Biochem., 72, 248–254. To determine the $Ca^{2+}$-ATPase and phospholamban (PLB) proteins 30 $\mu$g of total protein of each tissue sample was analyzed by SDS-PAGE (13%) according to Laemmli, U., (1970), Nature, 227, 680–685. Proteins were detected by Western blotting (Towbin, H. et al., (1979), Proc. Natl. Acad. Sci., USA, 76, 4350–4354), onto a 0.45 $\mu$m nitrocellulose membrane (Bio-Rad Laboratories). The membranes for detection of $Ca^{2+}$-ATPase protein were incubated with anti-SR $Ca^{2+}$ ATPase polyclonal antibody (1:500) followed by anti-rabbit IgG-POD secondary antibody. Alternatively anti-SR $Ca^{2+}$ ATPase monoclonal antibody (1:1000; Affinity Bioreagents) followed by anti-mouse IgG-POD was used for detection of the $Ca^{2+}$-ATPase.

The membranes for detection of PLB protein were incubated with anti-PLB monoclonal antibody (Upstate Biotechnology, Inc.) at a dilution of 1:1000, the membranes were further washed and incubated with anti-mouse IgG-POD. The membranes were developed by ECL immunodetection (Amersham Life Science) followed by TMB stabilized substrate for HPR (Promega Corp.).

Results

According to the Western blots the $Ca^{2+}$ ATPase is detected in all tissue samples. Western blots also revealed that PLB is found in the left ventricular myocardium and in the distal coronary artery. Based on our Western blots no PLB could be detected from tissue samples derived from the aorta and the proximal part of the coronary artery.

Experiment 4. Analysis of the presence of phospholamban mRNA in porcine heart tissues Methods To answer the question if the smooth muscle or endothelial cells of porcine coronary artery contained phospholamban (PLB) mRNA, Northern analysis was carried out of samples from three hearts pooled with respect to the presence of PLB mRNA using methods well known in the art. A small-scale RNA purification was carried out from tissue of the porcine left ventricular myocardium, aorta and coronary artery (proximal and more distal regions) by powdering 200–800 mg of the tissue under liquid nitrogen in a mortar. The powder was suspended into denaturing solution (4 M guanidinium thiocyanate, 25 mM sodium citrate, pH 7, 0.5% N-lauroylsarcosine, 0.1 M 2-mercaptoethanol). After acidic phenol/chloroform extraction total RNA was precipitated twice with isopropanol and finally dissolved in water. The concentration of RNAs in the resulting preparations was determined spectrofotometrically and their integrity was analyzed in non-denaturing agarose gel stained by ethidiumbromide.

The Northern analysis of PLB mRNA in these preparations was carried out using conventional methods (Sambrook, J., Fritsch, E. F., Maniatis, T. (1989), Molecular Cloning: A laboratory Manual, 2. ed., Cold Spring Harbor Laboratory Press, Cold Spring Harbor, N.Y.). Briefly, 10 µg and 20 µg of total RNA from each tissue was loaded into 1% formaldehyde/agarose gel. As a control 10 µg of RNA preparation derived from human heart muscle tissue was used, and commercially available RNA ladders (BRL, Gaithersburg, Md.) were used to assess the molecular weights of RNAs. After the transfer of the separated RNAs onto nylon filter (Hybond-N, Amersham, UK), the filter was hybridized with the $^{32}$P-labeled coding region of the human PLB gene. After hybridization the filter was washed in stringent conditions well-known to those skilled in the art, and exposed to Kodak X-Omat film.

Results

The results show that the left ventricular tissue of the porcine heart contains RNA which reacts with the PLB hybridization probe. A signal at the same position was also detected, albeit at much lower intensity, in the samples from porcine aorta and coronary artery tissues. Thus, these results support the view that PLB gene is active in porcine coronary artery tissue.

Experiment 5. The effects on the left ventricular pressure and coronary flow

Methods

Guinea-pigs of either sex weighing 300–400 g were used in the study. After the guinea-pig was sacrificed by a blow on the skull and decapitated the heart was rapidly excised. The heart was then rinsed in cold oxygenated perfusion buffer. A cannula was inserted into the aorta and secured with a ligature. Retrograde perfusion began as soon as the heart was placed in a thermostatically controlled moist chamber of the Langendorff apparatus. Modified Tyrode solution (37° C.), equilibrated in a thermostatically controlled bulb oxygenator with carbogen (95% $O_2$ and 5% $CO_2$) was used as a perfusion buffer. The composition of the Tyrode solution was (in mM): NaCl 135; $MgCl_2 \times 6H_2O$ 1; KCl 5; $CaCl_2 \times 2H_2O$ 2; $NaHCO_3$ 15; $Na_2HPO_4 \times 2H_2O$ 1; glucose 10; pH 7.3–7.4. The experiments were carried out under constant pressure condition (50 mmHg). After a short prestabilization (10 min) a latex balloon (size 4) was carefully placed into the left ventricle through the left pulmonary vein and the left atrium. The latex balloon was attached to a stainless-steel cannula coupled with a pressure transducer. The latex balloon, the cannula and the chamber of the pressure transducer were filled with ethylene glycol/water (1:1) mixture avoiding any air-bubble. The isovolumetric left ventricular pressure was recorded through the pressure transducer. The maximal positive and negative derivatives of the left ventricular pressure were calculated by using the digitized pressure signals. At the beginning of the experiment, the volume of the balloon was adjusted to obtain a diastolic pressure of approximately 5 mmHg. Coronary flow (ml/min) was continuously recorded by an electromagnetic flow meter with a flow probe inserted above the aortic cannula. The heart was paced at 250 beats/min with a coaxial electrode localized on the surface of the right atrium. Before starting the experiment, the heart was allowed to stabilise further for 30–50 min with vehicle (0.1% DMSO) to reach a stable coronary flow.

After 15 min baseline recording various concentrations of the test compound of Example 1c were added to the perfusion buffer at 15 min intervals. The concentration range of 0.3–30 µM was tested. The vehicle concentration (0.1% DMSO) was kept constant throughout the experiment.

Results

Figure 3A:
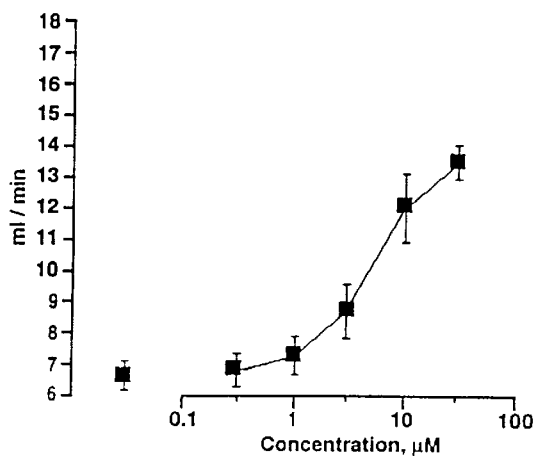
FIG. 3A shows the increase in coronary flow mediated through the direct dilatating effect of compound of Example 1c on the coronary arteries containing vascular smooth muscle cells and endothelial cells.
Figure 3B:
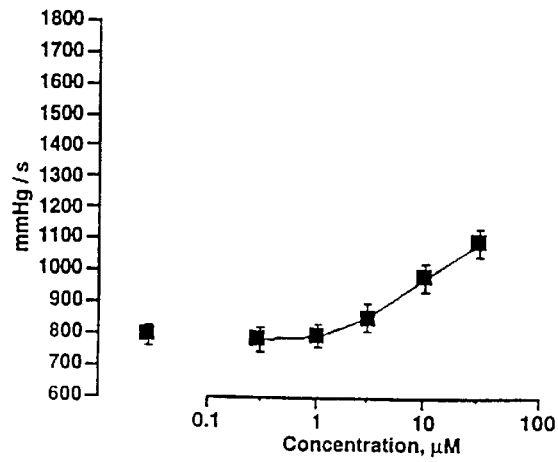
FIG. 3B shows the effect of compound of Example 1c on the positive derivative (positive dP/dt max) of the left ventricular pressure.
Figure 3C:
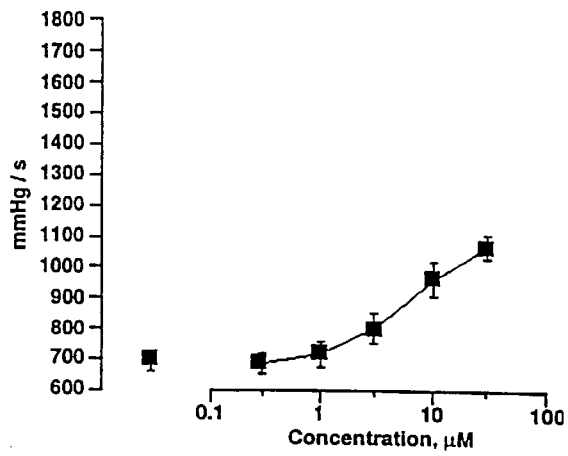
FIG. 3C shows the effect of compound of Example 1c on the negative derivative (negative dP/dt max) of the left ventricular pressure.

FIG. 3A shows the increase in coronary flow mediated through the direct dilatating effect of compound of Example 1c on the coronary arteries containing vascular smooth muscle cells and endothelial cells. FIGS. 3B and 3C show the effect of compound of Example 1c on the positive and negative derivatives (positive and negative dP/dt max) of the left ventricular pressure. Given are means ±SEM from six hearts paced at 250 beats/min.

It follows from the above experiments that the increase in coronary flow is mediated through the direct dilatating effect on the coronary arteries and that the dilatating effect is due to the inhibition of phospholamban present in the coronary arteries. Therefore the results suggest a potential use of phospholamban inhibitors in the treatment of patients who suffer from decreased coronary flow.

Table 2 shows EC50-values and maximum effects of various other phospholamban inhibitors of formula (I) or (II) on the coronary flow. Table 3 shows the $EC_{50}$ values and maximum effects (% change from baseline) of various compounds of the invention on left ventricular systolic pressure.

TABLE 2

EC50-values and maximum effects (% change from baseline) on the coronary flow.

| Compound of Example No. | EC50 (µM) | Maximum effect |
|---|---|---|
| 3c | 5 | +174% at 30 µM |
| 5c | >10 | +52% at 30 µM |
| 14c | 1.5 | +112% at 10 µM |
| 8g | 1 | +100% at 10 µM |
| 12 | 5 | +60% at 10 µM |
| 11b | 1 | +38% at 3 µM |
| 18e | 5 | +69% at 30 µM |
| 13d | 6 | +104% at 30 µM |
| 21 | 2 | +141% at 10 µM |
| 23 | 0.9 | +55% at 3 µM |

TABLE 3

The EC50 values and maximum effects (% change from baseline) on left ventricular systolic pressure.

| Compound of Example No. | EC$_{50}$ (μM) | maximum effect (%) |
|---|---|---|
| 1c | 9 | +52 at 30 μM |
| 3c | 4 | +63 at 10 μM |
| 5c | >10 | +14 at 30 μM |
| 6c | 0.5 | +25 at 10 μM |
| 7c | 2.5 | +29 at 10 μM |
| 8g | 2 | +64 at 10 μM |
| 9d | 5 | +50 at 30 μM |
| 12 | 5 | +22 at 10 μM |
| 13d | 10 | +48 at 30 μM |
| 14c | 1.5 | +25 at 10 μM |
| 15c | 3 | +37 at 10 μM |
| 169 | 10 | +57 at 30 μM |
| 18e | 10 | +35 at 30 μM |
| 19e | 6 | +39 at 30 μM |

Experiment 6.

This experiment demonstrate that the vasodilatory effect of the phospholamban inhibitor of Example 1c is due to an endothelial-mediated mechanism. Substance P, an endothelial-dependent vasodilator, was used as a reference compound. Triton×100 was used to destroy the endothelial cells of the coronary vessels.

The experiment was carried out under constant pressure condition (50 mmHg) on freely beating heart. Coronary flow (ml/min) was continuously recorded by an electromagnetic flow meter with a flow probe inserted above the aortic cannula.

Figure 4A:
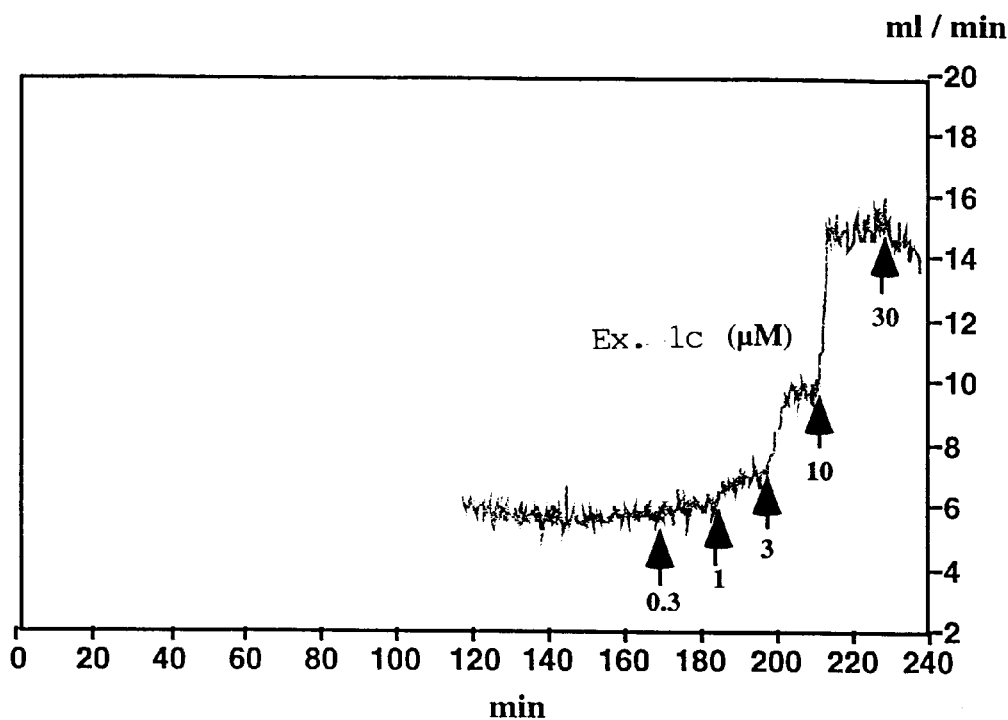
FIG. 4A shows the effect of compound of Example 1c on coronary flow (ml/min) without addition of Tritonx100.
Figure 4B:
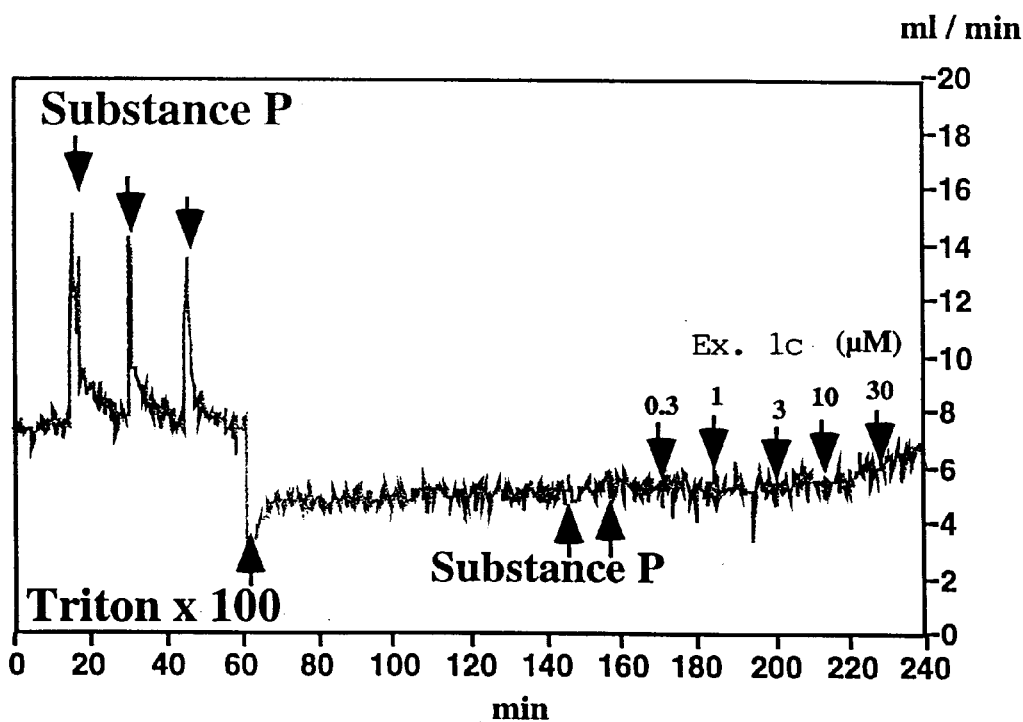
FIG. 4B shows the effect of compound of Example 1c on coronary flow (ml/min) with Tritonx100 used to destroy the endothelial cells of the coronary vessels.

After 15 min baseline recording a bolus dose of substance P (0.1 μM/0.3 ml) was added to the perfusion buffer via a side branch of the aortic cannula (FIG. 4B). The addition of substance P was repeated twice before the injection of triton×100 (0.05%/0.2 ml) was given via a needle inserted into the cannula just above the aorta. After 85 min of triton×100 injection a control dose of substance P was added twice to the perfusion buffer in order to check if the endothelial cells has destroyed. Thereafter the concentration range of 0.3–30 μM of the compound of Example 1c was tested. The vehicle concentration (0.1% DMSO) was kept constant throughout the experiment. A control experiment is shown in FIG. 4A where the effect of Example 1c is seen at the same concentration range when the endothelin is not disrupted by Triton×100.

Experiment 7. Effect on the development of stunned myocardium in isolated guinea-pig Langendorff heart
Method Guinea-pigs of either sex weighing 300–400 g were used in the study. After the guinea-pig was sacrificed by a blow on the skull and decapitated the heart was rapidly excised. The heart was then rinsed in oxygenated perfusion buffer. A cannula was inserted into the aorta and secured with a ligature. Retrograde perfusion began as soon as the heart was placed in a thermostatically controlled moist chamber of the Langendorff apparatus. Modified Tyrode solution (37° C.), equilibrated in a thermostatically controlled bulb oxygenator with carbogen (95% $O_2$ and 5% $CO_2$) was used as a perfusion buffer. The composition of the Tyrode solution was (in mM): NaCl 135; $MgCl_2 \times 6H_2O$ 1; KCl 5; $CaCl_2 \times 2H_2O$ 2; $NaHCO_3$ 15; $Na_2HPO_4 \times 2H_2O$ 1; glucose 10; pH 7.3–7.4. The experiments were carried out under constant pressure condition (50 mmHg). After a short prestabilization (10 min) a latex balloon attached through the stainless-steel cannula to a pressure transducer was carefully placed into the left ventricle through the left pulmonary vein and the left atrium. The latex balloon, the cannula and the chamber of the pressure transducer were filled with ethylene glycol/water (1:1) mixture avoiding any air-bubble. The isovolumetric left ventricular pressure was recorded through the pressure transducer. At the beginning of the experiment, the volume of the balloon was adjusted to obtain the end diastolic pressure of approximately 5 mmHg, Before starting the experiment, the spontaneously beating heart was allowed to stabilise further for 30–50 min with vehicle (0.1% DMSO) in the perfusion buffer.

Figure 5A:
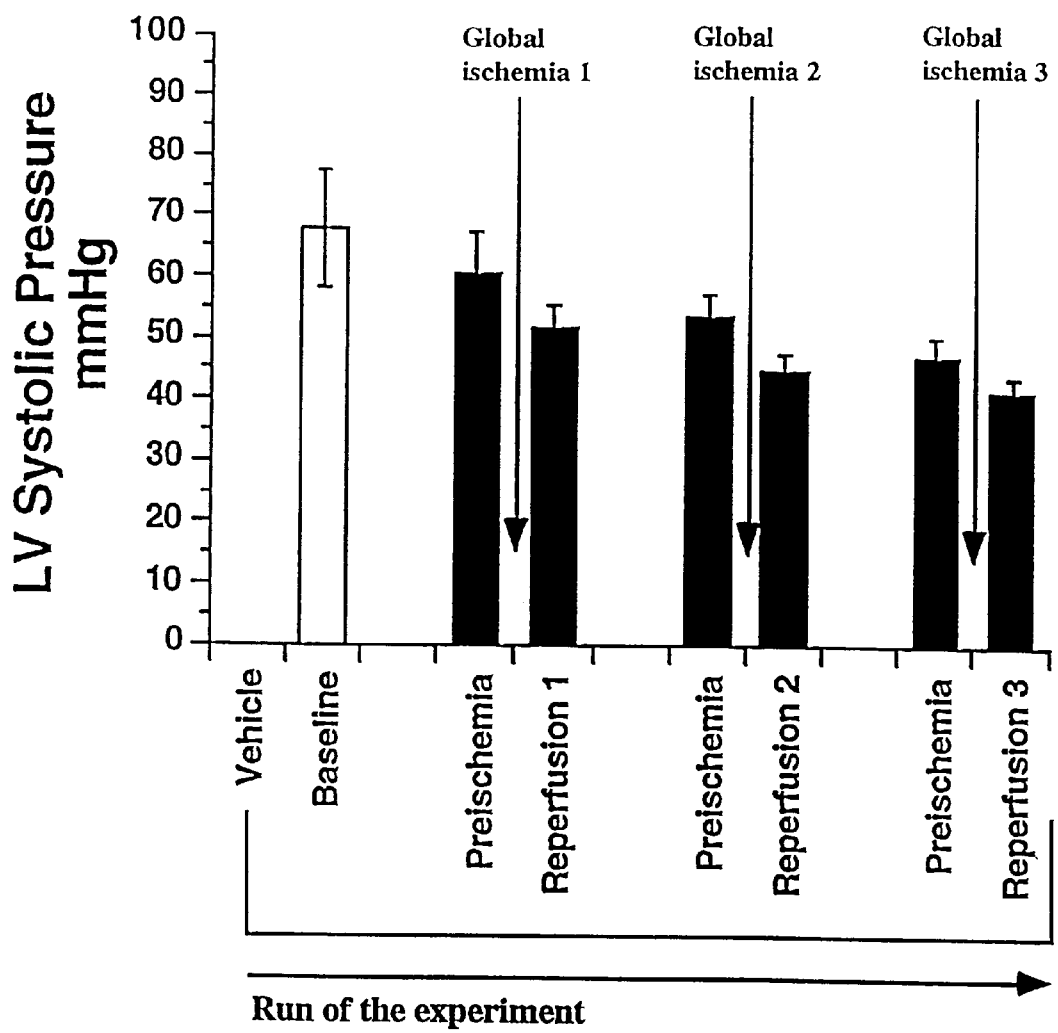
FIG. 5A shows the development of stunned myocardium and the subsequent decrease in the left ventricular systolic pressure.
Figure 5B:
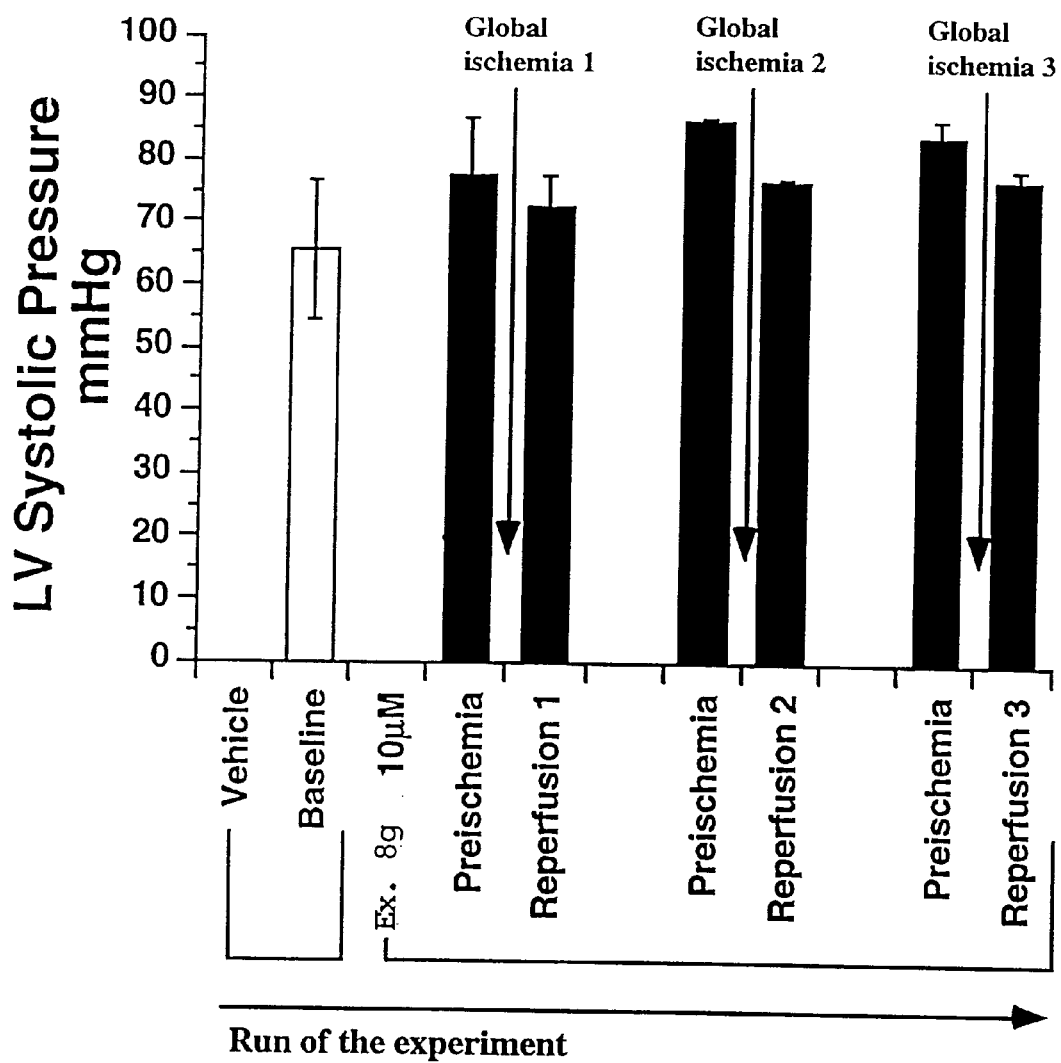
FIG. 5B shows the complete inhibition of the development of stunned myocardium by the compound of Example 8g.

After 15 min baseline recordings compound of Example 8 g (10 μM) was added to the perfusion buffer. The heart was 15 min later exposed to the 8 minute period of global ischemia followed by reperfusion. This procedure was then repeated twice at 35 min intervals. Another series of experiments was performed with vehicle instead of compound of Example 8 g. The vehicle concentration (0.1% DMSO) was kept constant throughout the experiments. The baseline value was the average of the two minute recordings obtained just before compound of Example 8 g or vehicle was added to the perfusion buffer. The preischemia values were the average of the two minute recordings obtained just before each ischemia period and the reperfusion values were the average of the two minute recordings obtained at 8 min during each reperfusion period. The results are shown in FIGS. 5A and B. FIG. 5A shows the development of stunned myocardium and the subsequent decrease in the left ventricular systolic pressure in the control group. FIG. 5B shows that the phospholamban inhibitor of Example 8 g completely inhibited the development of stunned myocardium. Givens are mean ±SEM of 2–3 experiments.

The following non-limiting examples illustrates the preparation of phospholamban inhibitors.

EXAMPLES

Example 1

Preparation of 3-Benzyl-5,7-bis[(1H-tetrazol-5-yl)methoxy]-4-methyl-2H-1-benzopyran-2-one a) 3-Benzyl-5,7-dihydroxy-4-methyl-2H-1-benzopyran-2-one

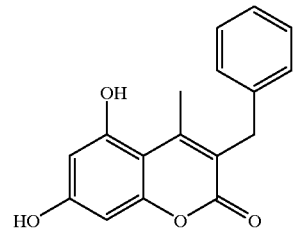

A solution of phloroglucinol dihydrate (20 g) and ethyl 2-benzylacetoacetate (27.5 ml) in ethanol (320 ml) was treated with dry HCl at 0° C. for five hours and the solution was kept at that temperature overnight. The yellow solution was concentrated and triturated with water, the solids filtered, washed with water and dried. The resulting hydrate was thrice evaporated to dryness from toluene, triturated with petroleum ether (bp. 40–60° C.) and filtered. Yield 33,4 g (96%). Melting point 258–260° C.

$^1$H-NMR (DMSO-d$_6$, 400 MHz): 2.525 (s, 3H, CH$_3$), 3.887 (s, 2 H, CH$_2$Ph), 6.171 (d, 1H, J=2,4 Hz), 6.274 (d, 1H, J=2,4 Hz), 7.167–7.279 (m, 5H, Ph), 10.2 (s,1H, OH), 10.47 (s, 1H, OH).

b) 3-Benzyl-5,7-bis(cyanomethoxy)-4-methyl-2H-1-benzopyran-2-one

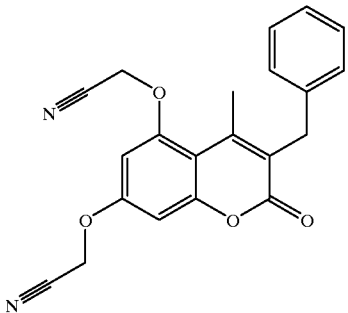

Chloracetonitrile (6.86 g), potassium carbonate (23.9 g) and 12.2 g of the product from example 1a were stirred in 120 ml of DMF at 100° C. under nitrogen for two hours. The reaction mixture was cooled and poured into ice water. The solids were filtered and washed with water. Yield 13.8 g (88%). Melting point 147–154° C.

$^1$H-NMR (DMSO-$d_6$, 400 MHz): 2.525 (s, 3H, CH$_3$), 3.969 (s, 2H, CH$_2$Ph), 5.307 (s, 2H, OCH$_2$CN), 5.314 (s, 2H, OCH$_2$CN), 6.814 (d,1 H, J=2.5 Hz), 6.940 (d, 1H, J=2.5 Hz), 7.18–7.292 (m, 5H, Ph).

c) 3-Benzyl-5,7-bis[(1H-tetrazol-5-yl)methoxy]-4-methyl-2H-1-benzopyran-2-one

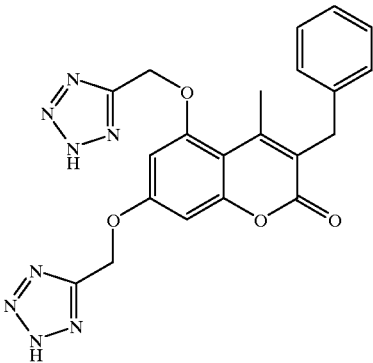

The product from example 1b (1 g), sodium azide (0.42 g) and ammonium chloride (0.34 g) were stirred in DMF (5 ml) under nitrogen at 100° C. for 5 hours. The reaction mixture was allowed to cool down and then poured into ice water. The pH of the solution was adjusted to 10–11 and then the solution either extracted once with ethyl acetate or filtered through CELITE. The solution was acidified to pH 2 with hydrochloric acid, kept at 5° C. and filtered. Yield 0.96 g (81%). Melting point 229–233° C.

$^1$H-NMR (DMSO-$d_6$, 400 MHz): 2.468 (s, 3H, CH$_3$), 3.937 (s, 2H, CH$_2$Ph), 5.596 (s, 2H, OCH$_2$Tet), 5.602 (s, 2H, OCH$_2$Tet), 6.832 (d, 1H, J=2.4 Hz), 6.851 (d, 1H, J=2.4 Hz), 7.171–7.283 (m, 5H, Ph).

Example 2

Preparation of 7,8,9,10-Tetrahydro-1,3-bis[(1H-tetrazol-5-yl)methoxy]-7-phenyl-6H-dibenzo[b,d]pyran-6-one a) 7,8,9,10-Tetrahydro-1,3-dihydroxy-7-phenyl-6H-dibenzo[b,d]pyran-6-one

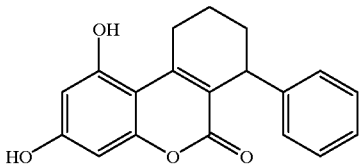

A solution of phloroglucinol (0.7 g) and 2-ethoxycarbonyl-3-phenylcyclohexanone (1.5 g) in ethanol was treated with dry HCl as described in example 1a. The product was first recrystallized from ethanol-water (1:1) and then triturated with ether. Yield 0.61 g.

$^1$H-NMR (DMSO-$d_6$, 400 MHz): 1.38–1.52 (m, 1H), 1.57–1.66 (m, 1H), 1.69–1.78 (m, 1H), 1.86–1.96 (m, 1H), 2.9–3.02 (m, 1H), 3.3–3.4 (m, 1H), 4.050 (b, 1H), 6.157 (d, 1H, J=2.4 Hz), 6.297 (d, 1H, J=2.4 Hz), 7.076–7.265 (m, 5H), 10.153 (s, 1H), 10.456 (s, 1H).

b) 7,8,9,10-Tetrahydro-1,3-bis(cyanomethoxy)-7-phenyl-6H-dibenzo[b,d]pyran-6-one

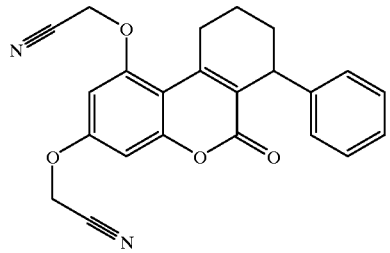

The product from example 2a (0.5 g) was treated with chloroacetonitrile (0.25 g) and potassium carbonate (1.12 g) in DMF (5 ml) as described in example 1b. Yield 0.6 g.

$^1$H-NMR (DMSO-$d_6$, 400 MHz): 1.38–1.58 (m, 1H), 1.6–1.7 (m, 1H), 1.7–1.76 (m, 1H), 1.89–1.99 (m, 1H), 2.9–3.03 (m, 1H), 3.2–3.28 (m 1H), 4.111 (b, 1H), 5.314 (s, 2H), 5.349 (s, 2H), 6.840 (d, 1H, J=2.5 Hz), 6.925 (d, 1H, J=2.5 Hz), 7.108–7.274 (m, 5H).

c) 7,8,9,10-Tetrahydro-1,3-bis[(1H-tetrazol-5-yl)methoxy]-7-phenyl-6H-dibenzo[b,d]pyran-6-one

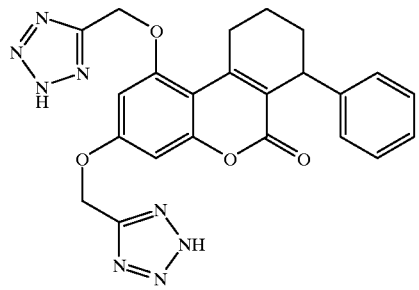

The product from example 2b (0.6 g) was treated with sodium azide (0.2 g) and ammonium chloride (0.17 g) in DMF (5 ml) as in example 1c. The product was recrystallized from a mixture of DMF, ethanol and water (approximately 1:2:3). Yield 0.41 g. Melting point: 153–154° C.

$^1$H-NMR (DMSO-d$_6$, 400 MHz): 1.38–1.5 (m, 1H), 1.5–1.6 (m, 1H), 1.69–1.76 (m, 1H), 1.87–1.96 (m, 1H), 2.9–3.05 (m, 1H), 3.2–3.3 (m, 1H), 4.094 (b, 1H), 5.602 (s, 2H), 5.643 (s, 2H), 6.832 (d, 1H, J=2.3 Hz), 6.851 (d, 1H, J=2.3. Hz), 7.089–7.212 (m, 5H).

Example 3

Preparation of 3-Benzyl-5,7-bis[(2,5-dihydro-5-oxo-4H-1,2,4-oxadiazol-3-yl)-methoxy]-4-methyl-2H-1-benzopyran-2-one a) 3-Benzyl-5,7-bis[(hydroxyamidino)methoxy]-4-methyl-2H-1-benzopyran-2-one

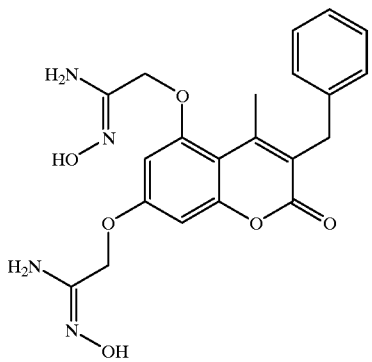

Triethylamine (1.94 ml) was added to a suspension of hydroxylamine hydrochloride (0.97 g) in DMSO (2 ml) and the resulting mixture stirred at room temperature for thirty minutes. The crystals were filtered and washed with THF. The filtrate was concentrated and the product from example 1b (0.5 g) added. This solution was kept at 75° C. overnight. The reaction mixture was treated with ice water, the pH adjusted to 11 and the solids filtered, washed with water, and dried. Yield 0.5 g. Melting point: 155–160° C.

$^1$H-NMR (DMSO-d$_6$, 400 MHz): 2.56 (s, 3H, CH$_3$), 3.938 (s, 2H), 4.466 (s, 2H), 4.486 (s, 2H), 5.565 (s, H, NH$_2$), 5.709 (s, 2H, NH$_2$), 6.658 (d, 1H, J=2.4 Hz), 6.692 (d, 1H, J=2.4 Hz), 7.168–7.284 (m, 5H, Ph), 9.346 (s, 1H, OH), 9.362 (s, 1H, OH).

b) 3-Benzyl-5,7-bis[(ethoxycarbonyloxyamidino)methoxy]-4-methyl-2H-1-benzopyran-2-one

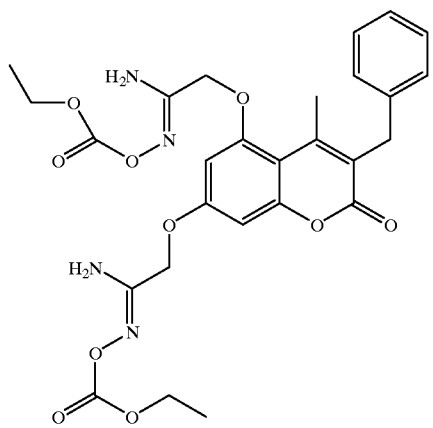

Ethyl chloroformiate (0.45 ml) was added to a solution of the product from example 3a (1 g) and pyridin (0.38 ml) in DMF (5 ml) at 0° C. The reaction mixture was kept at that temperature for an additional 30 minutes and then ice water added. The solids were filtered and washed with water. Yield 1.63 g. Melting point 87–92° C.

$^1$H-NMR (DMSO-d$_6$, 400 MHz): 1.215–1.256 (m, 6H), 2.553 (s, 3H), 3.947 (s, 2H), 4.140–4.198 (m, 4H), 4.566 (s, 2H), 4.599 (s, 2H), 6.688 (d, 1H, J=2.4 Hz), 6.718 (d, 1H, J=2.4 Hz), 6.792 (b, 2H, NH$_2$), 6.818 (b, 2H NH$_2$), 7.171–7.285 (m, 5H).

c) 3-Benzyl-5,7-bis[(2,5-dihydro-5-oxo-4H-1,2,4-oxadiazol-3-yl)methoxy]-4-methyl-2H-1-benzopyran-2-one

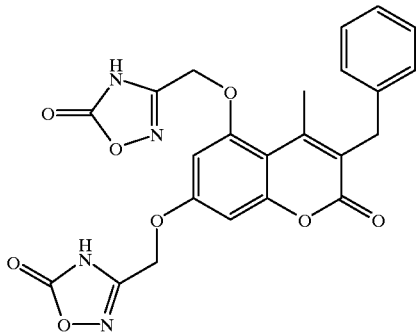

The product from the previous example (1.5 g) and DBU (0.8 ml) in DMF (5 ml) was stirred at room temperature overnight. The reaction mixture was treated with ice water and acidified. The solids were filtered and washed with water. The resulting solid mass was taken in 0.1 N sodium hydroxide solution, treated with activated carbon and finally acidified. Yield 0.64 g. Melting point: 130–136° C.

$^1$H-NMR (DMSO-d$_6$, 400 MHz): 2.524 (s, 3H), 3.954 (s, 2H), 5.187 (s, 2H), 5.215 (s, 2H), 6.748 (d, 1H, J=2.4 Hz), 6.834 (d, 1H, J=2.4 Hz), 7.158–7.289 (m, 5H), 12.8 (b, 2H).

Example 4

Preparation of 7,8,9,10-Tetrahydro-bis[(1H-tetrazol-5-yl)methoxy]-1,3-dihydroxy-6H-dibenzo[b,d]pyran-6-one a) 7,8,9,10-Tetrahydro-1,3-dihydroxy-6H-dibenzo[b,d]pyran-6-one

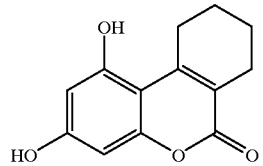

Phloroglucinol (1 g) and ethyl 2-oxocyclohexane carboxylate (1.32 g) were stirred in 75% sulfuric acid (10 ml) overnight, the mixture poured into ice water and filtered. Yield: 1.55 g.

$^1$H-NMR (DMSO-$d_6$, 400 MHz): 1.65 (b, 4H), 2.345 (b, 2H), 3.037 (b, 2H), 6.138 (d, 1H, J=2.4 Hz), 6.245 (d, 1H, J=2.4 Hz), 10.069 (b, 1H, OH), 10.322 (s, 1H, OH).

b) 7,8,9,10-Tetrahydro-bis(cyanomethoxy)-1,3-dihydroxy-6H-dibenzo[b,d]pyran-6-one

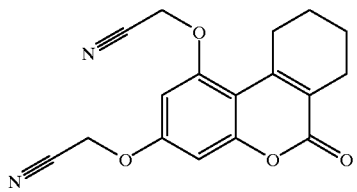

The product from the previous example (0.5 g), chloroacetonitrile (0.34 g) and potassium carbonate (1.5 g) in DMF (5 ml) were reacted as in example 1b. Yield: 0.44 g.

$^1$H-NMR (DMSO-$d_6$, 400 MHz): 1.68 (b, 4H), 2.41 (b, 2H), 3.00 (b, 2H), 5.297 (s, 2H), 5.309 (s, 2H), 6.797 (d, 1H, J=2.4 Hz), 6.899 (d, 1H, J=2.4 Hz).

c) 7,8,9,10-Tetrahydro-bis[(1H-tetrazol-5-yl)methoxy]-1,3-dihydroxy-6H-dibenzo[b,d]pyran-6-one

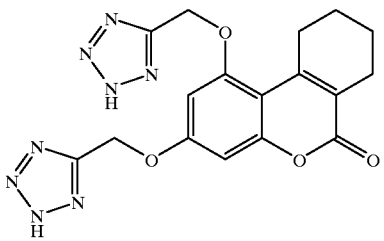

The product from the previous example (0.4 g) was treated with sodium azide (0.18 g) and ammonium chloride (0.14 g) in DMF (2.5 ml) as in example 1c. The product was recrystallized from ethanol-DMF (1:1). Yield 0.17 g. Melting point 283–286° C.

$^1$H-NMR (DMSO-$d_6$, 400 MHz): 1.626 (b, 4H), 2.393 (b, 2H), 2.971 (b, 2H), 5.583 (s, 2H), 5.599 (s, 2H), 6.811 (s, 2H).

Example 5

Preparation of 5,7-Bis[(1H-tetrazol-5-yl)methoxy]-4-phenyl-2H-1-benzopyran-2-one a) 5,7-Dihydroxy-4-phenyl-2H-1-benzopyran-2-one

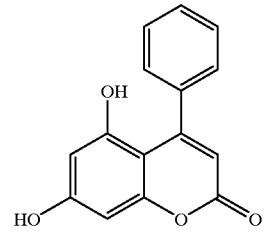

A solution of phloroglucinol (2.00 g) and ethyl benzoylacetate (3.05 g) in ethanol (30 ml) was treated with dry HCl as described in example 1a. The product was recrystallized from ethanol-water (1:1). Yield 3.0 g (75%).

$^1$H-NMR (DMSO-$d_6$, 300 MHz): 5.739 (s, 1H, CH=C), 6.155 (d, 1H, J=2.3 Hz), 6.263 (d, 1H, J=2.3 Hz), 7.305–7.381 (m, 5H, Ph), 10.084 (s, 1H, OH), 10.368 (s, 1H, OH).

b) 5,7-Bis(cyanomethoxy)-4-phenyl-2H-1-benzopyran-2-one

The product from previous example (1.00 g) was treated with chloroacetonitrile (0.62 g) and potassium carbonate (2.72 g) in DMF (5 ml) as described in example 1b. The reaction mixture was poured into ice water and the mixture extracted with ethyl acetate. Ethyl acetate was washed with 1 M NaOH, dried with sodium sulfate and evaporated. The product was recrystallized from isopropanol. Yield 0.41 g (31%).

$^1$H-NMR (DMSO-$d_6$, 300 MHz): 4.845 (s, 2H, OCH$_2$CN), 5.344 (s, 2H, OCH$_2$CN), 6.086 (s, 1H, CH=C), 6.770 (d, 1H, J=2.4 Hz), 7.040 (d, 1H, J=2.4 Hz), 7.320–7.443 (m, 5H, Ph).

c) 5,7-Bis[(1H-tetrazol-5-yl)methoxy]-4-phenyl-2H-1-benzopyran-2-one

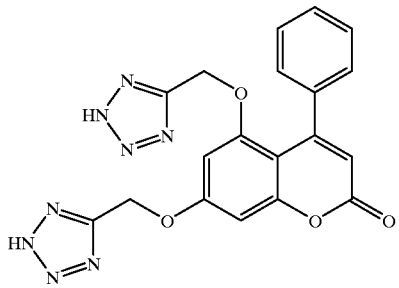

The product from previous example (0.40 g) was treated with sodium azide (0.16 g) and ammonium chloride (0.14 g) in DMF (2 ml) at 100° C. for 2 hours. The product was isolated as described in example 1c. Yield: 0.40 g (79%). Melting point 222–224° C.

$^1$H-NMR (DMSO-d$_6$, 400 MHz): 5.148 (s, 2H, OCH$_2$Tet), 5.649 (s, 2H, OCH$_2$Tet), 5.968 (s, 1H, CH=C), 6.811 (d, 1H, J=2.3 Hz), 6.962 (d, 1H, J=2.3 Hz), 6.994–7.185 (m, 5H, Ph).

Example 6

Preparation of 7,8,9,10-Tetrahydro-1,3-bis[(1H-tetrazol-5-yl)methoxy]-8-phenyl-6H-dibenzo[b,d]pyran-6-one a) 7,8,9,10-Tetrahydro-1,3-dihydroxy-8-phenyl-6H-dibenzo[b,d]pyran-6-one

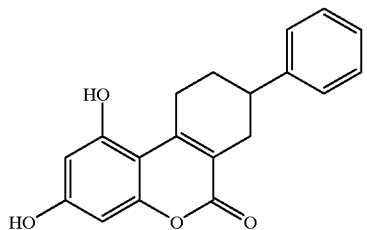

A solution of phloroglucinol (1.56 g) and ethyl 2-oxo-5-phenylcyclohexane-carboxylate (2.52 g) in ethanol (25 ml) was treated with dry HCl as described in example 1a. The precipitate was filtered and washed with water and EtOH. Yield 1.0 g (32%).

$^1$H-NMR (DMSO-d$_6$, 400 MHz): 1.72–1.82 (m, 1H), 2.01 (b, 1H), 2.317–2.387 (m, 1H), 2.707–2.763 (m, 1H), 2.830 (b, 1H), 3.041 (b, 1H), 3.35 and 3.40 (b, 1H), 6.174 (d, 1H, J=2.3 Hz), 6.277 (d, 1H, J=2.3 Hz), 7.200–7.350 (m, 5H, Ph), 10.131 (s, 1H, OH), 10.401 (s, 1H, OH).

b) 7,8,9,10-Tetrahydro-1,3-bis(cyanomethoxy)-8-phenyl-6H-dibenzo[b,d]pyran-6-one

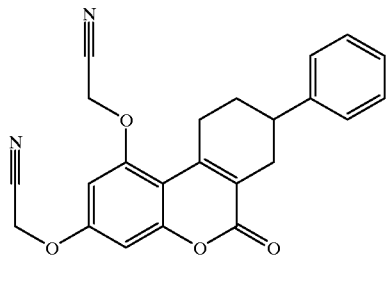

The product from previous example (1.0 g) was treated with chloroacetonitrile (0.57 g) and potassium carbonate (1.0 g) in DMF (5 ml) as described in example 1b. DMF was evaporated and residue dissolved in EtOAc. Ethyl acetate was washed with 1 M NaOH, dried with sodium sulfate and evaporated. The product was recrystallized from acetone-isopropanol (1:3). Yield 0.50 g (40%).

$^1$H-NMR (DMSO-d$_6$, 300 MHz): 1.75–1.88 (m, 1H), 2.05 (b, 1H), 2.38–2.48 (m, 1H), 2.77–2.85 (m, 1H), 2.90 (b, 1H), 3.07 (b, 1H), 3.22 and 3.28 (b, 1H), 5.316 (s, 2H, OCH$_2$CN), 5.331 (s, 2H, OCH$_2$CN), 6.829 (d, 1H, J=2.5 Hz), 6.939 (d, 1H, J=2.5 Hz), 7.210–7.380 (m, 5H, Ph).

c) 7,8,9,10-Tetrahydro-1,3-bis[(1H-tetrazol-5-yl)methoxy]-8-phenyl-6H-dibenzo[b,d]pyran-6-one

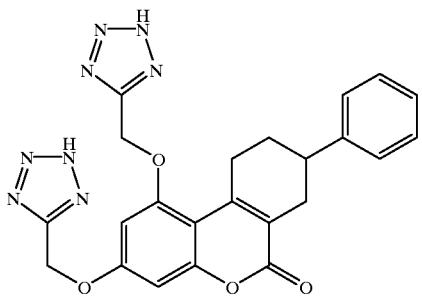

The product from previous example (0.30 g) was treated with sodium azide (0.10 g) and ammonium chloride (0.09 g) in DMF (2 ml) at 100° C. for 3.5 hours. The product was isolated in the same manner as in example 1c. Yield 0.30 g (82%). Melting point 235–245° C.

$^1$H-NMR (DMSO-d$_6$, 400 MHz): 1.70–1.80 (m, 1H), 1.96 (b, 1H), 2.38–2.446 (m, 1H), 2.836 (m, 2H), 3.052 (b, 1H), 3.252 and 3.301 (b, 1H), 5.604 (s, 2H, OCH$_2$CN), 5.632 (s, 2H, OCH$_2$CN), 6.827 (d, 1H, J=2.5 Hz), 6.858 (d, 1H, J=2.5 Hz), 7.209–7.351 (m, 5H, Ph).

Example 7

Preparation of 5,7-Bis[(1H-tetrazol-5-yl)methoxy]-4-methyl-3-(2-phenylethyl)-2H-1benzopyran-2-one a) 5,7-Dihydroxy-4-methyl-3-(2-phenylethyl)-2H-1-benzopyran-2-one

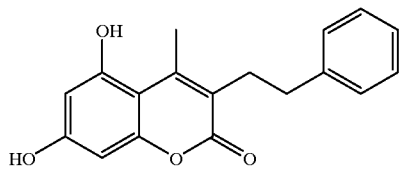

A solution of phloroglucinol (0.87 g) and ethyl 2-(2-phenylethyl)acetoacetate (1.62 g) in ethanol (30 ml) was treated with dry HCl as described in example 1a. Yield: 1.77 g (87%). Melting point 248–252° C.

$^1$H-NMR (DMSO-$d_6$, 300 MHz): 2.413 (s, 3H, CH$_3$), 2.652–2.782 (m, 4H, CH$_2$CH$_2$), 6.151 (d, 1H, J=2.4 Hz), 6.256 (d, 1H, J=2.4 Hz), 7.183–7.304 (m, 5H, Ph), 10.137 (s, 1H, OH), 10.369 (s, 1H, OH).

b) 5,7-Bis(cyanomethoxy)-4-methyl-3-(2-phenylethyl)-2H-1-benzopyran-2-one

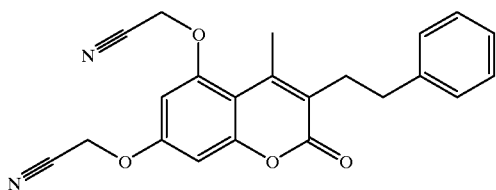

The product from previous example (0.90 g) was treated with chloroacetonitrile (0.48 g) and potassium carbonate (2.1 g) in DMF (5 ml) at 100° C. for 0.5 hours. The product was isolated as described in example 1b. Yield 1.00 g (88%). Melting point 179–183° C.

$^1$H-NMR (DMSO-$d_6$, 300 MHz): 2.384 (s, 3H, CH$_3$), 2.699–2.754 (m, 2H, CH$_2$CH$_2$), 2.805–2.841 (m, 2H, CH$_2$CH$_2$), 5.302 (s, 4H, OCH$_2$CN), 6.790 (d, 1H, J=2.5 Hz), 6.909 (d, 1H, J=2.5 Hz), 7.190–7.307 (m, 5H, Ph).

c) 5,7-Bis[(1H-tetrazol-5-yl)methoxy]-4-methyl-3-(2-phenylethyl)-2H-1benzopyran-2-one

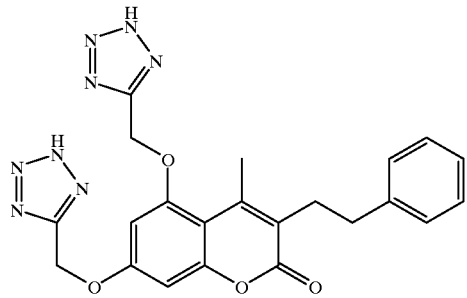

The product from previous example (0.40 g) was treated with sodium azide (0.15 g) and ammonium chloride (0.12 g) in DMF (2 ml) at 100° C. for 2.5 hours. The product was isolated as described in example 1c. Yield 0.385 g (78%). Melting point 248–250° C.

$^1$H-NMR (DMSO-$d_6$, 400 MHz): 2.368 (s, 3H, CH$_3$), 2.668–2.707 (m, 2H, CH$_2$CH$_2$), 2.783–2.822 (m, 2H, CH$_2$CH$_2$), 5.593 (s, 2H, OCH$_2$Tet), 5.604 (s, 2H, OCH$_2$Tet), 6.819 (d, 1H, J=2.3 Hz), 6.834 (d, 1H, J=2.3 Hz), 7.161–7.291 (m, 5H, Ph).

Example 8

Preparation of 5,7-Bis[(1H-tetrazol-5-yl)methoxy]-1,3-dibenzyl-4-methyl-2(1H)-quinolinone a) 2-Benzyl-3-oxobutanoic acid 3,5-dimethoxyanilid

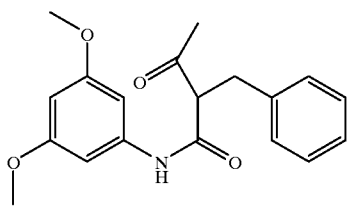

3,5-Dimethoxyaniline (5 g) was added in portions to a preheated (160° C.) ethyl 2-benzyl acetoacetate (15 ml) under nitrogen and kept at that temperature for 60 minutes. The cooled solution was diluted with heptane-ethyl ether and filtered. Yield 5.2 g (49%).

$^1$-H-NMR (DMSO-$d_6$, 300 MHz): 2.183 (s, 3H), 3.069 (d, 2H, J=7.2 Hz), 3.923 (t, 1H, J=7.2 Hz), 6.616 (dd. 1H, J=2.3 Hz), 6.765 (d, 2H, J=2.3 Hz), 7.13–7.3 (m, 5H), 10.123 (s, 1H).

b) 3-Benzyl-5,7-dimethoxy-4-methyl-2(1H)-quinolinone

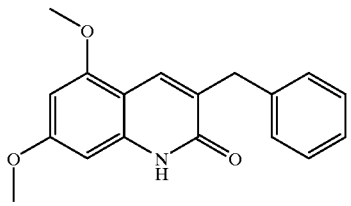

The product from the previous example (1.2 g) was added to a preheated (85° C.) methanesulfonic acid (3.5 ml) and kept at that temperature for 15 minutes. The solution was allowed to cool and then treated with ice water. The product was filtered, washed with sodium bicarbonate and water. Yield 1.08 g (95%).

$^1$-H-NMR (300 MHz):2.486 (s, 3H), 3.785 (s, 3H), 3.808 (s, 3H), 3.985 (s, 2H), 6.315 (d, 1H, J=2.4 Hz), 6.472 (d, 1H, J=2.4 Hz), 7.1–7.3 (m, 5H), 11.52 (s, 1H).

c) 3-Benzyl-5,7-dihydroxy-4-methyl-2(1H)-quinolinone

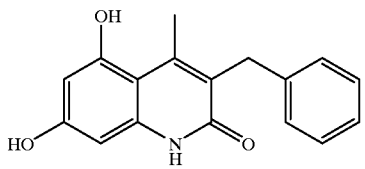

The product from the previous example (1 g) was refluxed under nitrogen in pyridine hydrochloride (5 g) for twenty minutes. The reaction mixture was treated with water and the product filtered. Yield 0.9 g (100%). Melting point: 307–312° C.

$^1$-H-NMR (300 MHz):2.503 (s, 3H), 3.942 (s, 2H), 6.102 (d, 1H, J=2.3 Hz), 6.187 (d, 1H, J=2.3 Hz), 7.1–7.25 (m, 5H), 9.725 (s, 1H), 9.984 (s, 1H), 11.285 (s, 1H).

d) 1,3-Dibenzy-5,7-dimethoxy-4-methyl-2(1H)-quinolinone

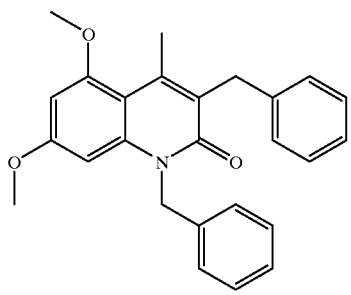

The product from the example 8b (1 g), potassium 1-butoxide (0.62 g) and benzyl bromide (0.68 ml) were stirred in DMSO (10 ml) at 60° C. for 4 hours. The reaction mixture was treated with water, extracted with toluene and evaporated. The product was triturated with ethyl ether and filtered. Yield 0.5 g (39%).

$^1$-H-NMR (400 MHz):2.537 (s, 3H), 3.708 (s, 3H), 3.826 (s, 3H), 4.124 (s, 2H), 5.56 (b, 2H), 6.413–6.434 (m, 2H), 7.154–7.332 (m, 10H).

e) 1,3-Dibenzyl-5,7-dihydroxy-4-methyl-2(1H)-quinolinone

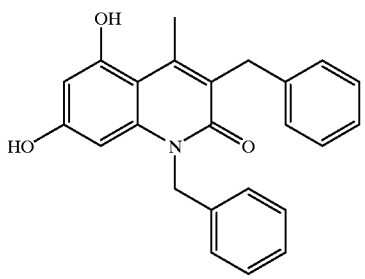

The product from the previous example (2 g) was treated with pyridine hydrochloride (10 g) as described in example 8c. The product was extracted with ethyl acetate and evaporated. Yield 1.4 g (75%).

$^1$-H-NMR (400 MHz):2.570 (s, 3H), 4.076 (s, 2H), 5.450 (b, 2H), 6.135 (d, 1H, J=2.2 Hz), 6.199 (d, 1H, J=2.2 Hz), 7.128–7.333 (m, 10H), 9.83 (b, 1H), 10.166 (s, 1H).

f) 5,7-Bis(cyanomethoxy)-1,3-dibenzyl-4-methyl-2(1H)-quinolinone.

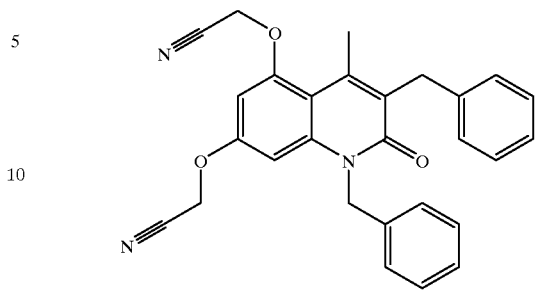

The product from the previous example (1.4 g) was treated with chloroacetonitrile (0.76 g) and $K_2CO_3$ (2.5 g) in DMF (20 ml) as described in example 1b. Yield 1.5 g (89%).

$^1$-H-NMR (400 MHz):2.555 (s, 3H), 4.146 (s, 2H), 5.214 (s, 2H), 5.275 (s, 2H), 5.578 (s, 2H), 6.735 (s, 2H), 7.13–7.33 (m, 10H).

g) 5,7-Bis[(1H-tetrazol-5-yl)methoxy]-1,3-dibenzyl-4-methyl-2(1H)-quinolinone

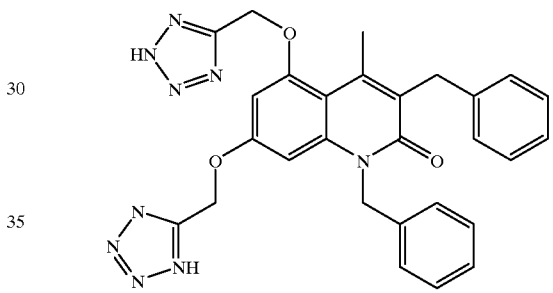

The product from the previous example (1.3 g) was treated with sodium azide (0.41 g) and ammonium chloride (0.34 g) as described in example 1c. Yield: 0.69 g (45%).

$^1$-H-NMR (400 MHz):2.471 (s, 3H), 4.113 (s, 2H), 5.477 (s, 2H), 5.55 (b, 2H), 5.574 (s, 2H), 6.670 (d, 1H, J=2.1 Hz), 6.775 (d, 1H, J=2.1 Hz), 7.13–7.32 (m, 10H).

Example 9

Preparation of 5,7-Bis[(1H-tetrazol-5-yl)methoxy]-3-benzyl-1,4-dimethyl-2(1H)-quinolinone a) 3-Benzyl-5,7-dimethoxy-1,4-dimethyl-2(1H)-quinolinone

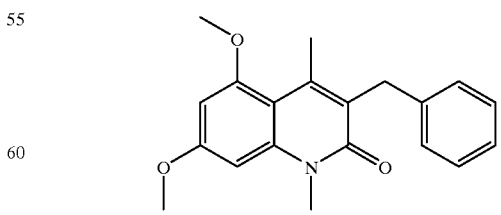

The product from example 8b (0.5 g), t-BuOK (0.2 g) and methyl iodide (0.4 ml) were stirred in DMSO (5 ml) at 35° C. for two days. The reaction mixture was treated with water and extracted with toluene. The product was purified by column chromatography using toluene-ethyl acetate-acetic acid 8:2:1 as the eluent. Yield 0.24 g (46%).

$^1$-H-NMR (300 MHz):2.51 (s, 3H), 3.632 (s, 2H), 3.846 (s, 3H), 3.896 (s, 3H), 4.047 (s, 2H), 6.468 (d, 1H, J=2.3 Hz), 6.558 (d, 1H, J=2.3 Hz), 7.1–7.26 (m, 5H).

b) 3-Benzyl-5,7-dihydroxy-1,4-dimethyl-2(1H)-quinolinone

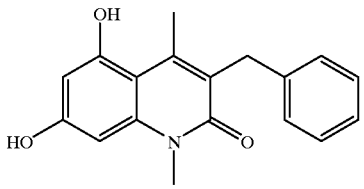

The product from the previous example (0.2 g) was treated with pyridine hydrochloride (2 g) as described in example 8c and the product extracted with ethyl acetate. Yield 0.16 g (89%).

$^1$-H-NMR (400 MHz):2.567 (s, 3H), 3.515 (s, 3H), 4.005 (s, 2H), 6.244 (d, 1H, J=2.3 Hz), 6.268 (d, 1H, J=2.3 Hz), 7.08–7.25 (m. 5H), 9.879 (s, 1H), 10.113 (s, 1H).

c) 5,7-Bis(cyanomethoxy)-3-benzyl-1,4-dimethyl-2(1H)-quinolinone

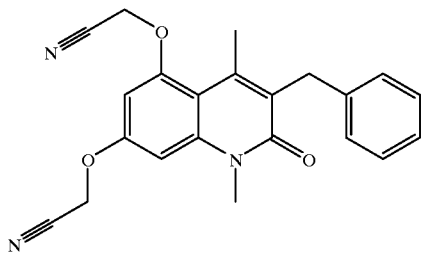

The product from the previous example (0.15 g), chloroacetonitrile 0.08 g) and $K_2CO_3$ (0.28 g) were reacted in DMF (2 ml) as described in example 1b. Yield 0.16 g (84%).

$^1$-H-NMR (400 MHz): 2.524 (s, 3H), 3.658 (s, 3H), 4.079 (s, 2H), 5.292 (s, 2H), 5.379 (s, 2H), 6.766 (d, 1H, J=2.3 Hz), 6.855 (d, 1H, J=2.3 Hz), 7.13–7.24 (m 5H).

d) 5,7-Bis[(1H-tetrazol-5-yl)methoxy]-3-benzyl-1,4-dimethyl-2(1H)-quinolinone

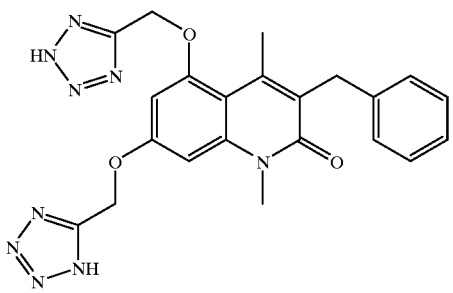

The product from the previous example (0.15 g) was treated with $NaN_3$ (57 mg) and $NH_4Cl$ (47 mg) in DMF (2 ml) as described in example 1c. Yield 0.115 g. Melting point: 250–253° C.

$^1$-H-NMR (400 MHz): 2.451 (s, 3H), 3.649 (s, 3H), 4.042 (s, 2H), 6.792 (d, 1H, J=2.2 Hz), 6.833 (d, 1H, J=Hz), 7.1–7.25 (m, 5H).

Example 10

Preparation of 3-Benzyl-5,7-bis[(2-methyl-1H-tetrazol-5-yl)methoxy]-4-methyl-2H-1-benzopyran-2-one and the three isomers

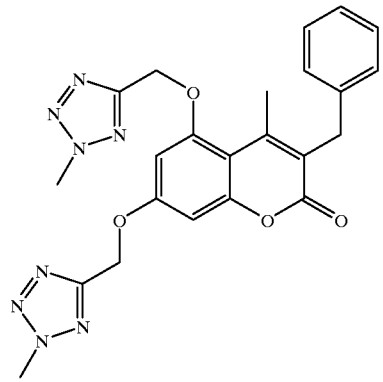

0.07 ml of methyl iodide was added to a solution of 0.2 g of the product from example 1c and 0.31 g of $K_2CO_3$ in 2 ml of DMF and the mixture stirred at room temperature for 4 hours. The reaction mixture was poured into ice water and filtered. Yield 0.2 g as a mixture of four regioisomers, melting point 71–76° C.

$^1$H-NMR (DMSO-$d_6$, 400 MHz): 2.47 (s, $CH_3$), 2.48 (s, $CH_3$), 3.93 (s, $CH_2Ph$), 4.11 (s, $NCH_3$), 4.12 (s, $NCH_3$), 4.15 (s, $NCH_3$), 4.38 (s, $NCH_3$), 4.40 (s, $NCH_3$), 5.51 (s, $OCH_2$), 5.52 (s, $OCH_2$), 5.62 (s, $OCH_2$), 5.67 (s, $OCH_2$), 6.84–6.91 (m, 2H), 7.16–7.28 (m,5H, Ph).

Example 11

Preparation of 3-Benzyl-5,7-bis[1-(1H-tetrazol-5-yl)ethoxy]4-methyl-2H-1-benzopyran-2-one, mixture of stereoisomers a) 3-Benzyl-5,7-bis-[(1-cyano)ethoxy)-4-methyl-2H-1-benzopyran-2-one

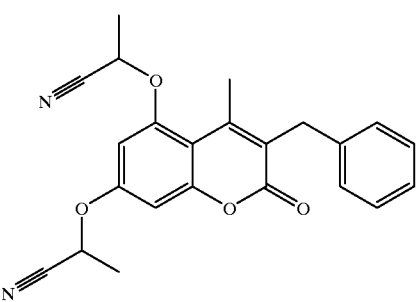

The product from example 1a (1 g), 2-chlorpropionitrile (0.7 g) and potassium carbonate (2 g) were heated in DMF (15 ml) under nitrogen at 110° C. for sixty minutes. The mixture was treated with water, filtered and washed with 1 N NaOH and water. Yield 1.2 g.

$^1$H-NMR (DMSO-$d_6$, 300 MHz): 1.74–1.78 (t+t, 6 H, CH—$CH_3$), 2.53 (s, 3 H), 3.97 (s, 2H), 5.58–5.66 (m, 2H, CH—$CH_3$), 6.87 (m, 1H), 6.99 (d, 1H), 7.18–7.31 (m, 5H).

b) 3-Benzyl-5,7-bis[1-(1H-tetrazol-5-yl)ethoxy]4-methyl-2H-1-benzopyran-2-one, mixture of stereoisomers

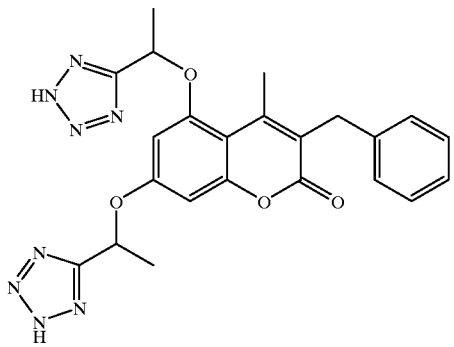

The product from the previous example (0.5 g), sodium azide (0.18 g) and ammonium chloride (0.15 g) were heated in DMF (7 ml) at 100° C. for 90 minutes. The product was treated with water, extracted with ethyl acetate and evaporated. Yield 0.57 g. Melting point 91–104° C.

$^1$H-NMR (DMSO-d$_6$, 300 MHz): 1.69–1.77 (m, 6 H, CH—CH$_3$), 2.54 (s, 3H), 3.94 (s, 2H), 6.10–6.17 ((m, 2H, CH—CH$_3$), 6.65 (dd, 1H), 6.74 (dd, 1H), 7.13–7.30 (m, 5H).

Example 12

Preparation of 5,7-Bis(carboxymethoxy)-1,3-dibenzyl-4-methyl-2(1H)-quinolinone

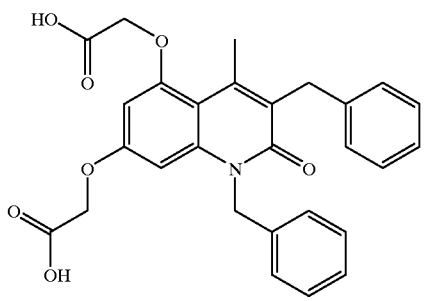

The product from example 8f (0.2 g) was refluxed in a solution of concentrated hydrochloric acid (3 ml) and acetic acid (2 ml) for one hour. The product was filtered at 25° C. Yield 0.14 g.

$^1$H-NMR (300 Mhz, DMSO-d$_6$): 2.63 (s, CH3), 4.14 (s, 2H, CH$_2$Ph), 4.66 (s, 2 H, OCH$_2$COOH), 4.79 (s, 2H, OCH$_2$COOH), 5.53 (s, 2H, NCH$_2$Ph), 6.41 (d, 1H, J=2.2 Hz), 6.45 (d, 1H, J=2.2 Hz), 7.13–7.34 (m, 10 H, Ph).

Example 13

Preparation of 3-Benzyl-5,7-bis[(1H-tetrazol-5-yl)methoxy]-1-(4-fluorobenzyl)-4-methyl-2(1H)-quinolinone a) 1-Benzyl-5,7-dimethoxy-3-(4-fluorobenzyl)-4-methyl-2(1H)-quinolinone

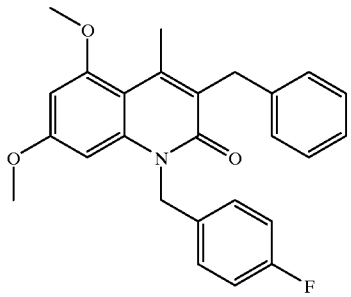

The product from example 8b (2 g), potassium-tert-butoxide (0.87 g) and 4-fluorobenzylchloride (1.12 g) were heated in DMSO (20 ml) at 60° C. for three hours as in example 8d. Yield 1.28 g.

$^1$H-NMR (400 Mhz, DMSO-d$_6$): 2.53 (s, 3H), 3.73 (s, 3H), 3.83 (s, 3H), 5.55 (s, 2H), 6.43 (s, 2H), 7.12–7.2 (m, 5 H), 7.26–7.28 (m, 4H).

b) 3-Benzyl-5,7-dihydroxy-1-(4-fluorobenzyl)-4-methyl-2(1H)-quinolinone

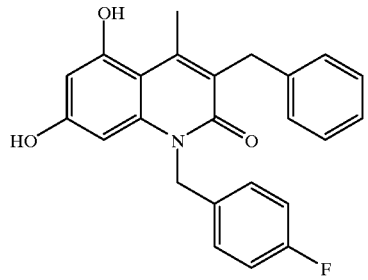

The product from previous example (1.25 g) were heated in pyridine hydrochloride (12.5 g) at about 225° C. for 9 minutes. Yield 1 g.

$^1$H-NMR (300 Mhz, DMSO-d$_6$): 2.56 (s, 3H), 4.07 (s, 2H), 5.4 (b, 2H), 6.13 (d, 1H, J=2.1 Hz), 6.20 (d, 1H, J=2.1 Hz), 7.12–7.28 (m, 9H), 9.88 (s, 1H), 10.22 (s, 1H).

c) 3-Benzyl-5,7-Bis(cyanomethoxy)-1-(4-fluorobenzyl)-4-methyl-2(1H)-quinolinone

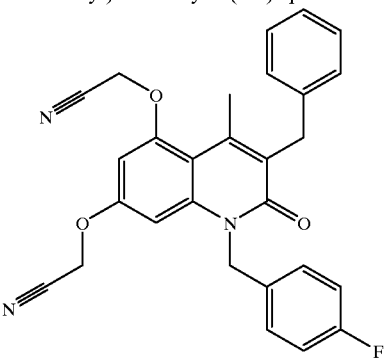

The product from the previous example (1 g), ClCH$_2$CN (0.43 g) and K$_2$CO$_3$ (1.42 g) were heated in DMF (8 ml) at 120° C. for one hour. Yield 0.94 g.

$^1$H-NMR (300 Mhz, DMSO-d$_6$): 2.55 (s, 3H), 4.14 (s, 2H), 5.25 (s, 2H), 5.28 (s, 2H), 5.57 (s, 2H), 6.74 (s, 2H, ArH), 7.1–7.3 (m, 9H).

d) 3-Benzyl-5,7-bis[(1H-tetrazol-5-yl)methoxy]-1-(4-fluorobenzyl)-4-methyl-2(1H)-quinolinone

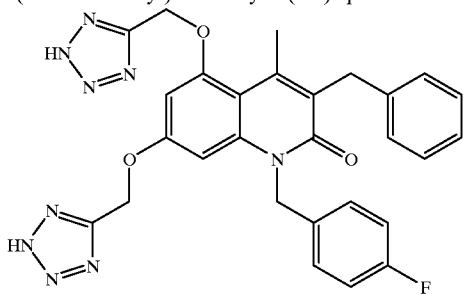

The product from the previous example (0.5 g), sodium azide (0.14 g) and ammonium chloride (0.12 g) were heated in DMF (5 ml) at 120° C. for 90 min. The product was triturated with acetonitrile. Yield 0.28 g. Melting point: 126–132° C.

$^1$H-NMR (300 Mhz, DMSO-d$_6$): 2.48 (s, 3H), 4.11 (s, 2H), 5.51 (s, 2H), 5.55 (s, 2H), 5.58 (s, 2H), 6.67 (d, 1H, J=2.1 Hz), 6.78 (d, 1H, J=2.1 Hz).

Example 14

Preparation of 5,7-Bis[(1H-tetrazol-5-yl)methoxy]-3-(4-chlorobenzyl)-4-methyl-2H-1-benzopyran-2-one a) 3-(4-Chlorobenzyl)-5,7-dihydroxy-4-methyl-2H-1-benzopyran-2-one

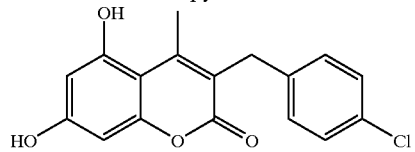

A solution of phloroglucinol (1.57 g) and ethyl 2-(4-chlorobenzyl)acetoacetate (3.18 g) in ethanol (25 ml) was treated with dry HCl at 0° C. for 1.5 hours and the solution was kept at that temperature overnight. Solvent was evaporated and the precipitate triturated with water. Yield 3.87 g (98%). Melting point 270–278° C.

$^1$H-NMR (DMSO-d$_6$, 300 MHz): 2.52 (s, 3H, CH$_3$), 3.87 (s, 2H, CH$_2$), 6.17 (d, 1H, J=2.4 Hz), 6.28 (d, 1H, J=2.4 Hz), 7.18–7.34 (m, 4H, Ph), 10.21 (s, 1H, OH), 10.48 (s, 1H, OH).

b) 5,7-Bis(cyanomethoxy)-3-(4-chlorobenzyl)-4-methyl-2H-1-benzopyran-2-one

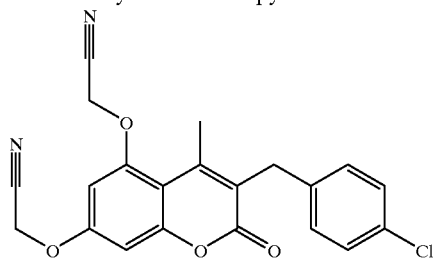

The product from the previous example (1.00 g), chloroacetonitrile (0.50 g) and potassium carbonate (2.18 g) were heated in DMF (5 ml) at 100° C. for 30 minutes. The product was isolated as described in example 1b. Yield 0.90 g (72%).

$^1$H-NMR (DMSO-d$_6$, 300 MHz): 2.52 (s, 3H, CH$_3$), 3.95 (s, 2H, CH$_2$), 5.308 (s, 2H, OCH$_2$CN), 5.312 (s, 2H, OCH$_2$CN), 6.81 (d, 1H, J=2.5 Hz), 6.94 (d, 1H, J=2.5 Hz), 7.22–7.33 (m, 4H, Ph).

c) 5,7-Bis[(1H-tetrazol-5-yl)methoxy]-3-(4-chlorobenzyl)-4-methyl-2H-1-benzopyran-2-one

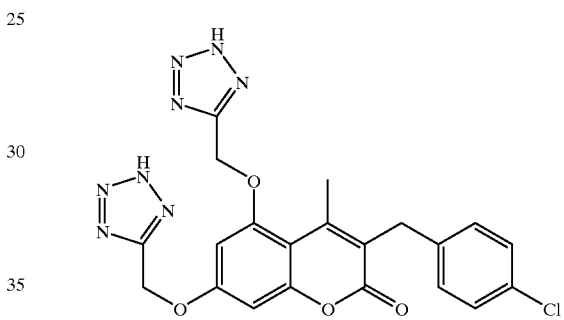

The product from the previous example (0.40 g), sodium azide (0.14 g) and ammonium chloride (0.11 g) were heated in DMF (2 ml) at 100° C. for 2 hours. The product was isolated as in example 1c. Yield 0.40 g (82%).

$^1$H-NMR (DMSO-d$_6$, 300 MHz): 2.46 (s, 3H, CH$_3$), 3.92 (s, 2H, CH$_2$), 5.602 (s, 2H, OCH$_2$Tet), 5.609 (s, 2H, OCH$_2$Tet), 6.83 (d, 1H, J=2.5 Hz), 6.85 (d, 1H, J=2.5 Hz), 7.20–7.33 (m, 4H, Ph).

Example 15

Preparation of 5,7-Bis[(1H-tetrazol-5-yl)methoxy]-3-(4-nitrobenzyl)-4-methyl-2H-1-benzopyran-2-one a) 5,7-Dihydroxy-4-methyl-3-(4-nitrobenzyl)-2H-1-benzopyran-2-one

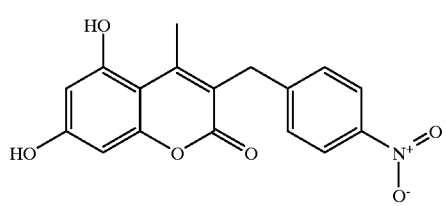

A solution of phloroglucinol (0.48 g) and ethyl 2-(4-nitrobenzyl)acetoacetate (1.00 g) in ethanol (150 ml) was treated with dry HCl at 0° C. for 7.5 hours and the solution was kept at that temperature overnight. Solvent was evaporated and the precipitate triturated with water. Yield 0.63 g (51%). Melting point 280–285° C.

$^1$H-NMR (DMSO-$d_6$, 300 MHz): 2.53 (s, 3H, $CH_3$), 4.03 (s, 2H, $CH_2$), 6.19 (d, 1H, J=2.4 Hz), 6.29 (d, 1H, J=2.4 Hz), 7.40–7.51 and 8.11–8.17 (m, 4 H, Ph), 10.25 (s, 1H, OH), 10.52 (s, 1H, OH).

b) 5,7-Bis(cyanomethoxy)-3-(4-nitrobenzyl)-4-methyl-2H-1-benzopyran-2-one

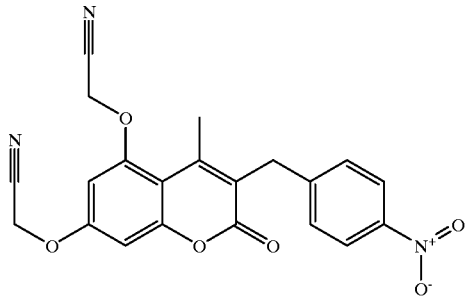

The product from the previous example (0.57 g), chloroacetonitrile (0.27 g) and potassium carbonate (1.20 g) were heated in DMF (2 ml) at 100° C. for 50 minutes. The product was isolated as described in example 1b. Yield 0.47 g (67%). Melting point 178–185° C.

$^1$H-NMR (DMSO-$d_6$, 400 MHz): 2.53 (s, 3H, $CH_3$), 4.11 (s, 2H, $CH_2$), 5.319 (s, 2H, $OCH_2CN$), 5.323 (s, 2H, $OCH_2CN$), 6.83 (d, 1H, J=2.4 Hz), 6.96 (d, 1H, J=2.4 Hz), 7.48–7.53 and 8.12–8.16 (m, 4H, Ph).

c) 5,7-Bis[(1H-tetrazol-5-yl)methoxy]-3-(4-nitrobenzyl)-4-methyl-2H-1-benzopyran-2-one

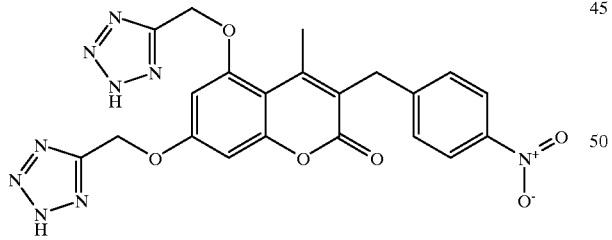

The product from the previous example (0.38 g), sodium azide (0.12 g) and ammonium chloride (0.11 g) were heated in DMF (3 ml) at 100° C. for 2 hours. The product was isolated as described in example 1c. Yield 0.25 g (54%). Melting point 240–244° C.

$^1$H-NMR (DMSO-$d_6$, 400 MHz): 2.47 (s, 3H, $CH_3$), 4.08 (s, 2H, $CH_2$), 5.611 (s, 2H, $OCH_2Tet$), 5.623 (s, 2H, $OCH_2Tet$), 6.85 (d, 1H, J=2.4 Hz), 6.87 (d, 1H, J=2.4 Hz), 7.46–7.50 and 8.12–8.16 (m, 4H, Ph).

Example 16

Preparation of 5,7-Bis[(1H-tetrazol-5-yl)methoxy]-3-cyclopentyl-4-methyl-2H-1-benzopyran-2-one a) 3-Cyclopentyl-5,7-dihydroxy-4-methyl-2H-1-benzopyran-2-one

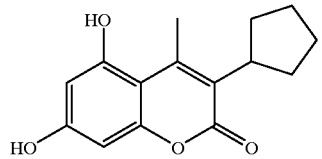

A solution of phloroglucinol (2.00 g) and ethyl 2-cyclopentylacetoacetate (3.14 g) in ethanol (40 ml) was treated with dry HCl at 0° C. for 2.5 hours and the solution kept at that temperature overnight. Solvent was evaporated and the precipitate purified with flash chromatography eluting with toluene-EtOAc-AcOH (8:1:1). Yield 1.22 g (29%).

$^1$H-NMR (DMSO-$d_6$, 300 MHz): 1.50–1.88 (m, 8H, —$(CH_2)_4$—), 2.57 (s, 3H, $CH_3$), 3.25 (m, 1H, CH), 6.11 (d, 1H, J=2.4 Hz), 6.25 (d, 1H, J=2.4 Hz), 10.25 (b, 2H, OH).

b) 5,7-Bis(cyanomethoxy)-3-cyclopentyl-4-methyl-2H-1-benzopyran-2-on

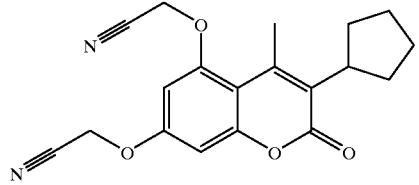

The product from the previous example (0.50 g), chloroacetonitrile (0.31 g) and potassium carbonate (0.61 g) were heated in DMF (2 ml) at 80° C. for 40 minutes. The product was isolated as described in example 1b. Yield 0.56 g (86%).

$^1$H-NMR (DMSO-$d_6$, 300 MHz): 1.55–1.90 (m, 8H, —$(CH_2)_4$—), 2.56 (s, 3H, $CH_3$), 3.37 (m, 1H, CH), 5.29 (s, 2H, $OCH_2CN$), 5.31 (s, 2H, $OCH_2CN$), 6.75 (d, 1H, J=2.5 Hz), 6.88 (d, 1H, J=2.5 Hz).

c) 5,7-Bis[(1H-tetrazol-5-yl)methoxy]-3-cyclopentyl-4-methyl-2H-1-benzopyran-2-one

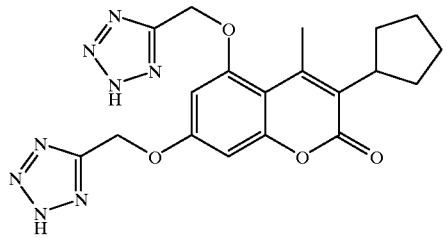

The product from the previous example (0.30 g), sodium azide (0.13 g) and ammonium chloride (0.11 g) were heated in DMF (1 ml) at 100° C. for 1.5 hours. The product was isolated as described in example 1c. Yield 0.30 g (80%). Melting point 248–252° C.

$^1$H-NMR (DMSO-$d_6$, 400 MHz): 1.53–1.89 (m, 8H, —$(CH_2)_4$—), 2.51 (s, 3H, $CH_3$), 3.34 (m, 1 H, CH), 5.59 (s, 2H, $OCH_2Tet$), 5.61 (s, 2H, $OCH_2Tet$), 6.80 (s, 2H).

Example 17

Preparation of 5,7-Bis[(1H-tetrazol-5-yl)methoxy]-4-methyl-3-(1-naphtylmethyl)-2H-1-benzopyran-2-one a) 5,7-dihydroxy-4-methyl-3-(1-naphtylmethyl)-2H-1-benzopyran-2-one

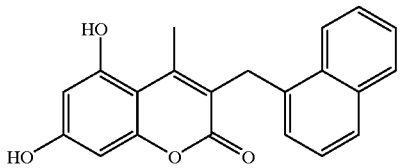

A solution of phloroglucinol (0.47 g) and ethyl 2-(1-naphtylmethyl)acetoacetate (1.00 g) in ethanol (20 ml) was treated with dry HCl at 0° C. for 3 hours and the solution kept at that temperature overnight. Solvent was evaporated and the precipitate triturated with water and recrystallized from isopropanol-water (1:1). Yield 0,96 g (78%). Melting point 275–280° C.

$^1$H-NMR (DMSO-$d_6$, 400 MHz): 2.45 (s, 3H, CH$_3$), 4.32 (s, 2H, CH$_2$), 6.23 (d, 1H, J=2.5 Hz), 6.32 (d, 1 H, J=2.5 Hz), 6.97–8.25 (m, 7H, Naph), 10.26 (s, 1H, OH), 10.53 (s,1H, OH).

b) 5,7-Bis(cyanomethoxy)-4-methyl-3-(1-naphtylmethyl)-2H-1-benzopyran-2-one

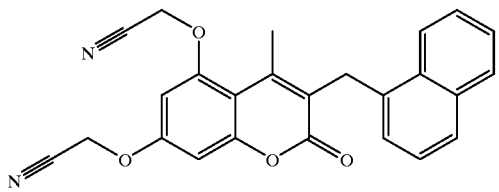

The product from the previous example (0.80 g), chloroacetonitrile (0.36 g) and potassium carbonate (0.66 g) were heated in DMF (4 ml) at 100° C. for 1 hour. The product was isolated as described in example 1b. Yield 0.30 g (30%).

$^1$H-NMR (DMSO-$d_6$, 300 MHz): 2.45 (s, 3H, CH$_3$), 4.40 (s, 2H, CH$_2$), 5.34 (s, 2H, OCH$_2$CN), 5.36 (s, 2H, OCH$_2$CN), 6.86 (d, 1H, J=2.5 Hz), 7.010 (d, 1H, J=2.5 Hz), 7.016–8.27 (m, 7H, Naph).

c) 5,7-Bis[(1H-tetrazol-5-yl)methoxy]-4-methyl-3-(1-naphtylmethyl)-2H-1-benzopyran-2-one

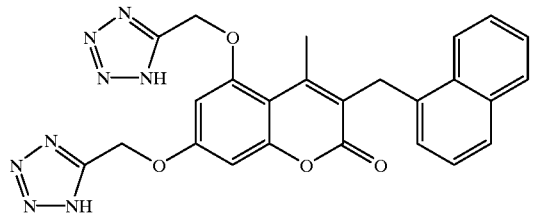

The product from the previous example (0.25 g), sodium azide (0.080 g) and ammonium chloride (0.072 g) were heated in DMF (2 ml) at 100° C. for 2.5 hours. The product was isolated as described in example 1c. Yield 0.11 g (36%). Melting point 164–174° C.

$^1$H-NMR (DMSO-$d_6$, 300 MHz): 2.40 (s, 3H, CH$_3$), 4.37 (s, 2H, CH$_2$), 5.63 (s, 2H, OCH$_2$Tet), 5.65 (s, 2H, OCH$_2$Tet), 6.87 (d, 1H, J=2.5 Hz), 6.92 (d, 1H, J=2.5 Hz), 6.98–8.26 (m, 7H, Naph).

Example 18

Preparation of 1-Benzyl-5,7-bis-[(1H-tetrazol-5-yl)-methoxy]-4-methyl-2(1H)-quinolinone a) 5,7-Dimethoxy-4-methyl-2(1H)-quinolinone

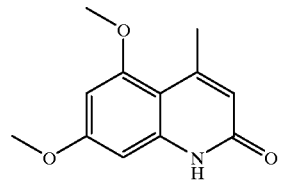

tert-Butyl acetoacetate (1.58 g) was heated to 120° C. and 3,5-dimethoxyaniline (1.53 g) dissolved in xylene (4 ml) was added. The mixture was heated at 120–130° C. for 20 minutes and then cooled to room temperature. Methanesulfonic acid (2 ml) was added and the mixture was stirred at ambient temperature for 10 minutes. Water (40 ml) was added and the precipitate filtered and dried. Yield 1.31 g (60%).

$^1$H-NMR (DMSO-$d_6$, 300 MHz): 2.50 (s, 3H, CH$_3$), 3.79 (s, 3H, OCH$_3$), 3.83 (s, 3H, OCH$_3$), 6.03 (s, 1H, CH=C), 6.31 (d, 1H, J=2.3 Hz), 6.45 (d, 1H, J=2.3 Hz), 11.4 (b, 1H, NH).

b) 1-Benzyl-5,7-dimethoxy-4-methyl-2(1H)-quinolinone

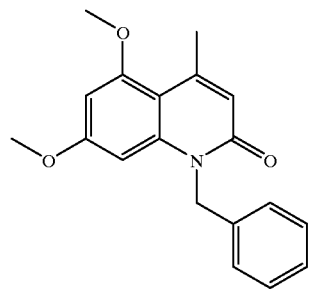

The product from the previous example (1.20 g) was suspended to DMSO (15 ml) and t-BuOK (0.68 g) and benzylbromide (1.03 g) were added. Reaction mixture was stirred at ambient temperature overnight. Water was added and the product extracted to EtOAc. EtOAc was dried and evaporated to dryness. The product was recrystallized from toluene. Yield 0.80 g (47%).

$^1$H-NMR (DMSO-$d_6$, 300 MHz): 2.55 (d, 3H, J=1.1 Hz, CH$_3$), 3.71 (s, 3H, OCH$_3$), 3.84 (s, 3H, OCH$_3$), 5.48 (b, 2H, NCH$_2$), 6.29 (d, 1H, J=1.1 Hz, CH=C), 6.4 (s, 2H), 7.18–7.33 (m, 5H, Ph).

c) 1-Benzyl-5,7-dihydroxy-4-methyl-2(1H)-quinolinone

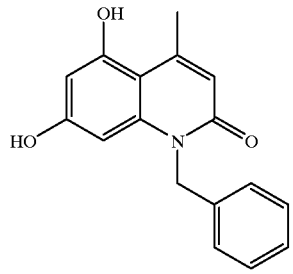

The product from the previous example (0.69 g) was dissolved to $CH_2Cl_2$ (14 ml) and the reaction mixture cooled to −20° C. $BBr_3$ (2.4 g) in $CH_2Cl_2$ (1M solution) was added and the mixture was allowed to warm to ambient temperature during the night. The precipitate was filtered, washed with $CH_2Cl_2$ and dissolved to EtOAc. EtOAc was washed with dilute HCl, dryed and evapotated to dryness. Yield 0.34 g (54%).

$^1$H-NMR (DMSO-$d_6$, 300 MHz): 2.56 (d, 3H, J=1.0 Hz, $CH_3$), 5.33 (b, 2H, $NCH_2$), 6.11 (d, 1H, J=2.1 Hz), 6.13 (d, 1H, J=1.0 Hz, CH═C), 6.17 (d, 1H, J=2.1 Hz), 7.12–7.34 (m, 5H, Ph), 9.90 (b, 1H, OH), 10.22 (s, 1H, OH).

d) 1-Benzyl-5,7-bis(cyanomethoxy)-4-methyl-2(1H)-quinolinone

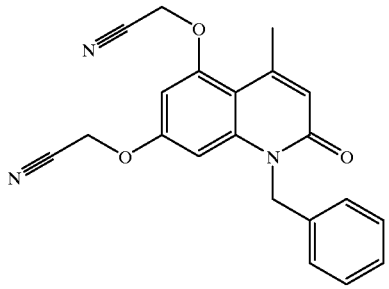

The product from the previous example (0.34 g), chloroacetonitrile (0.13 g) and potassium carbonate (0.34 g) were heated in DMF (2 ml) at 100° C. for 1.5 hours. Water was added and the precipitate filtered and dried. The product was recrystallized from isopropanol. Yield 0.20 g (46%).

$^1$H-NMR (DMSO-$d_6$, 400 MHz): 2.57 (s, 3H, $CH_3$), 5.22 (s, 2H, $OCH_2CN$), 5.30 (s, 2H, $OCH_2CN$), 5.50 (b, 2H, $NCH_2$), 6.42 (s, 1H, CH═C), 6.70 (d, 1H, J=2.1 Hz), 6.73 (d, 1H, J=2.1 Hz), 7.21–7.32 (m, 5H, Ph).

e) 1-Benzyl-5,7-bis-[(1H-tetrazol-5-yl)methoxy]-4-methyl-2(1H)-quinolinone

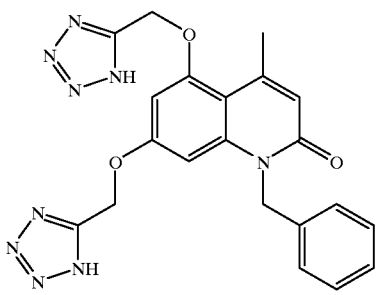

The product from the previous example (0.20 g), sodium azide (0.072 g) and ammonium chloride (0.060 g) were heated in DMF (2 ml) at 100° C. for 3 hours. The product was isolated as described in example 1c. Yield 0.21 g (85%). Melting point 246–249° C.

$^1$H-NMR (DMSO-$d_6$, 400 MHz): 2.50 (s, 3H, $CH_3$), 5.48 (b, 4H, $OCH_2Tet$, $NCH_2$), 5.60 (s, 2H, $OCH_2Tet$), 6.34 (s, 1H, CH═C), 6.64 (d, 1H, J=1.9 Hz), 6.77 (d, 1H, J=1.9 Hz), 7.18–7.32 (m, 5H, Ph).

Example 19

Preparation of 1-Benzyl-5,7-bis[1H-tetrazol-5-yl)methoxy]-3-(2-fluorobenzyl)-4-methyl-2(1H)-quinolinone a) 5,7-Dimethoxy-3-(2-fluorobenzyl)-4-methyl-2(1H)-quinolinone

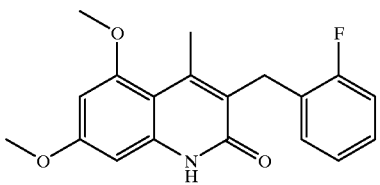

Ethyl 2-(2-fluorobenzyl)acetoacetate (2.5 g) in xylene (1 ml) was heated to 150° C. and 3,5-dimethoxyaniline (1.46 g) in xylene (4 ml) was added in small portions during 30 minutes. The reaction mixture was heated at 160° C. for 3 hours and then cooled to room temperature. Methanesulfonic acid (1.7 ml) was added and the mixture was stirred at ambient temperature for 30 minutes. Water was added and the precipitate filtered and dried. The product was triturated with warm ethanol. Yield 0.64 g (21%).

$^1$H-NMR (DMSO-$d_6$, 300 MHz): 2.45 (s, 3H), 3.79 (s, 3H), 3.82 (s, 3H), 3.97 (s, 2H), 6.33 (d, 1H, J=2.4 Hz), 6.48 (d, 1H, J=2.4 Hz), 6.90–7.25 (m, 4H), 11.61 (s, 1H).

b) 1-Benzyl-5,7-dimethoxy-3-(2-fluorobenzyl)-4-methyl-2(1H)-quinolinone

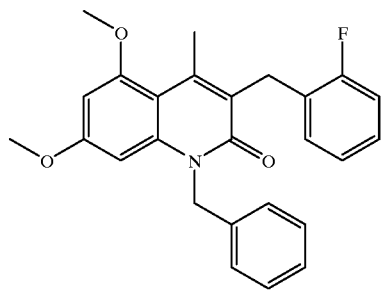

The product from the previous example (0.62 g) was treated with t-BuOK (0.23 g) and benzylbromide (0.36 g) in DMSO (12 ml) at 60° C. for 2.5 hours. The product was isolated as described in example 18b. Yield 0.39 g (49%).

$^1$H-NMR (DMSO-$d_6$, 400 MHz): 2.51 (s, 3H), 3.72 (s, 3H), 3.84 (s, 3H), 4.11 (s, 2H), 5.55 (b, 2H), 6.433 (d, 1H, J=2.1 Hz), 6.443 (d, 1H, J=2.1 Hz), 6.97–7.33 (m, 9H).

c) 1-Benzyl-5,7-dihydroxy-3-(2-fluorobenzyl)-4-methyl-2(1H)-quinolinone

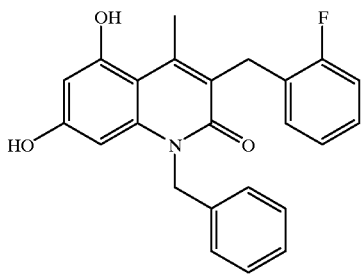

The product from the previous example (0.34 g) was treated with BBr$_3$ (8.48 g) in CH$_2$Cl$_2$ (7 ml) as in example 18c. Yield 0.30 g (82%).

$^1$H-NMR (DMSO-$d_6$, 400 MHz): 2.55 (s, 3H), 4.06 (s, 2H), 5.40 (b, 2H), 6.13 (d, 1H, J=2.1 Hz), 6.22 (d, 1H, J=2.1 Hz), 6.97–7.33 (m, 9H), 10.3 (b, 2H).

d) 1-Benzyl-5,7-bis(cyanomethoxy)-3-(2-fluorobenzyl)-4-methyl-2(1H)-quinolinone

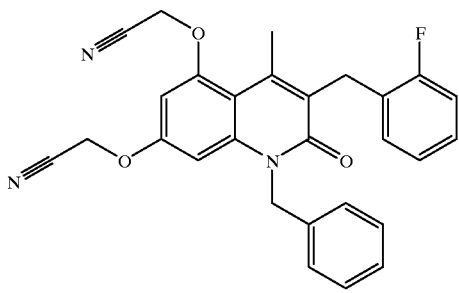

The product from the previous example (0.21 g), chloroacetonitrile (0.086 g) and potassium carbonate (0.37 g) were heated in DMF (2 ml) at 100° C. for 2 hours. The product was isolated as described in example 1b. Yield 0.18 g (71%).

$^1$H-NMR (DMSO-$d_6$, 400 MHz): 2.53 (s, 3H), 4.13 (s, 2H), 5.23 (s, 2H), 5.29 (s, 2H), 5.57 (b, 2H), 6.746 (d, 1H, J=2.3 Hz), 6.756 (d, 1H, J=2.3 Hz), 7.00–7.32 (m, 9H).

e) 1-Benzyl-5,7-bis[1H-tetrazol-5-yl)methoxy]-3-(2-fluorobenzyl)-4-methyl-2(1H)-quinolinone

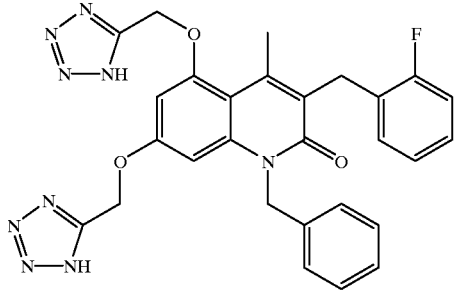

The product from the previous example (0.17 g), sodium azide (0.051 g) and ammonium chloride (0.042 g) were heated in DMF at 100° C. for 3 hours. The product was isolated as described in example 1c. Yield 0.17 g (85%). Melting point 135–140° C.

$^1$H-NMR (DMSO-$d_6$, 400 MHz): 2.46 (s, 3H), 4.10 (s, 2H), 5.48 (s, 2H), 5.51 (b, 2H), 5.59 (s, 2H), 6.68 (d, 1H, J=2.2 Hz), 6.79 (d, 1H, J=2.2 Hz), 6.99–7.32 (m, 9H).

Example 20

Preparation of 1-Benzyl-5,7-bis[1H-tetrazol-5-yl)methoxy]-4-methyl-3-(2-phenylethyl)-2(1H)-quinolinone a) 5,7-Dimethoxy-4-methyl-3-(2-phenylethyl)-2(1H)-quinolinone

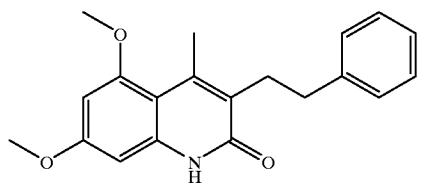

Ethyl 2-(2-phenylethyl)acetoacetate (2.70 g) in xylene (5 ml) was treated with 3,5-dimethoxyaniline (1.60 g) at 150° C. as described in example 19a. Methanesulfonic acid (4.0 ml) was added at room temperature and the mixture heated at 80° C. for 1 hour. The product was isolated as described in example 19a. Yield 1.38 g (41%).

$^1$H-NMR (DMSO-$d_6$, 400 MHz): 2.45 (s, 3H), 2.64–2.68 (m, 2H), 2.82–2.86 (m, 2H), 3.78 (s, 3H), 3.81 (s, 3H), 6.30 (d, 1H, J=2.3 Hz), 6.45 (d, 1H, J=2.3 Hz), 7.18–7.30 (m, 5H), 11.45 (s, 1H).

b) 1-Benzyl-5,7-dimethoxy-4-methyl-3-(2-phenylethyl)-2(1H)-quinolinone

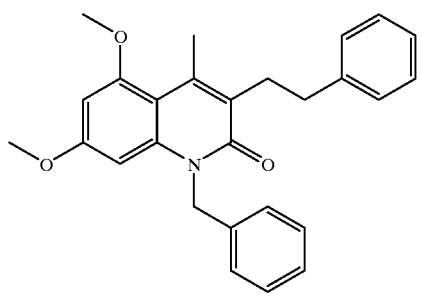

The product from the previous example (0.61 g), t-BuOK (0.24 g) and benzylbromide (0.36 g) were heated in DMSO (12 ml) at 60° C. for 2 hours. The product was isolated as described in example 18b. Yield 0.31 g (40%).

$^1$H-NMR (DMSO-$d_6$, 400 MHz): 2.51 (s, 3H), 2.73–2.77 (m, 2H), 2.96–3.00 (m, 2H), 3.70 (s, 3H), 3.83 (s, 3H), 5.55 (b, 2H), 6.40 (s, 2H), 7.17–7.33 (m, 10 H).

c) 1-Benzyl-5,7-dihydroxy-4-methyl-3-(2-phenylethyl)-2(1H)-quinolinone

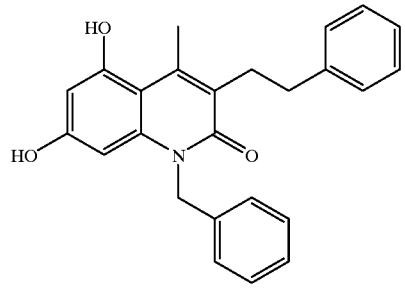

The product from the previous example (0.31 g) was treated with BBr$_3$ (0.75 g) in CH$_2$Cl$_2$ (5 ml) as described in example 18c. Yield 0.26 g (89%).

$^1$H-NMR (DMSO-$d_6$, 300 MHz): 2.56 (s, 3H), 2.69–2.75 (m, 2H), 2.90–2.95 (m, 2H), 5.39 (b, 2H), 6.08 (d, 1H, J=2.0 Hz), 6.19 (d, 1H, J=2.0 Hz), 7.11–7.33 (m, 10H), 10.2 (b, 2H).

d) 1-Benzyl-5,7-bis(cyanomethoxy)-4-methyl-3-(2-phenylethyl)-2(1H)-quinolinone

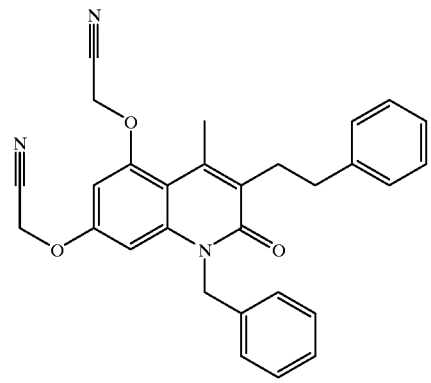

The product from the previous example (0.22 g), chloroacetonitrile (0.091 g) and potassium carbonate (0.39 g) were heated at 100° C. for 2 hours. The product was isolated as in example 1b. Yield 0.20 g (76%).

$^1$H-NMR (DMSO-$d_6$, 400 MHz): 2.50 (s, 3H), 2.73–2.77 (m, 2H), 2.98–3.02 (m, 2H), 5.21 (s, 2H), 5.29 (s, 2H), 5.56 (b, 2H), 6.70 (d, 1H, J=2.1 Hz), 6.72 (d, 1H, J=2.1 Hz), 7.18–7.33 (m, 10H).

e) 1-Benzyl-5,7-bis[1H-tetrazol-5-yl)methoxy]-4-methyl-3-(2-phenylethyl)-2(1H)-quinolinone

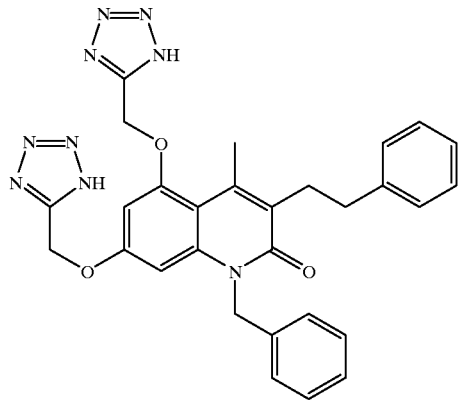

The product from the previous example (0.19 g), sodium azide (0.057 g) and ammonium chloride (0.047 g) were heated in DMF at 100° C. for 3 hours. The product was isolated as described in example 1c. Yield 0.18 g (78%). Melting point 215–218° C.

$^1$H-NMR (DMSO-$d_6$, 400 MHz): 2.46 (s, 3H), 2.70–2.74 (m, 2H), 2.95–2.99 (m, 2H), 5.47 (s, 2H), 5.54 (b, 2H), 5.57 (s, 2H), 6.64 (d, 1H, J=2.0 Hz), 6.77 (d, 1H, J=2.0 Hz), 7.16–7.33 (m, 10H).

Example 21

Preparation of 5,7-Bis(aminocarbonylmethoxy)-1,3-dibenzyl-4-methyl-2(1H)-quinolinone

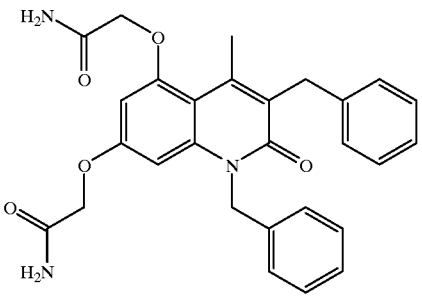

The mixture of 5,7-dihydroxy-1,3-dibenzyl-4-methyl-2(1H)-quinolinone (0.5 g), potassium carbonate (0.9 g) and 2-chloroacetamide (0.25 g) in DMF (6.5 ml) were reacted at 100° C. for two hours. The reaction mixture was treated with ice water and filtered. The product was triturated with hot ethanol. Yield: 0.32 g. Melting point 252–253° C.

$^1$H-NMR (400 MHz, DMSO-$d_6$): 2.63 (s, 3H, CH3), 4.13 (s, 2H, PhCH$_2$), 4.37 (s, 2H, OCH$_2$), 4.55 (s, 2H, OCH$_2$), 5.54 (s, 2H, NCH$_2$Ph), 6.40 (d, 1H, J=2 Hz, ArH), 6.53 (d, 1H, J=2 Hz, ArH), 7.13–7.33 (m, 10 H, Ph), 7.44 (d, 2H, J=65 Hz, CONH$_2$), 7.47 (d, 2H, J=68 Hz, CONH$_2$)

Example 22

Preparation of 5,7-Bis(ethoxycarbonylmethoxy)-1,3-dibenzyl-4-methyl-2(1H)-quinolinone

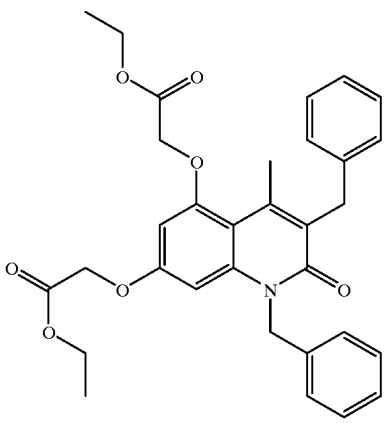

The mixture of 5,7-dihydroxy-1,3-dibenzyl-4-methyl-2(1H)-quinolinone (1 g), ethyl 2-bromoacetate (0.63 ml) and potassium carbonate (1.49 g) in DMF (5 ml) was heated under nitrogen at 110° C. for three hours, poured into ice water and filtered. The resulting solid material was triturated with ether and filtered again. Yield: 1.03 g, melting point 113–116° C.

$^1$H-NMR (400 MHz, DMSO-$d_6$): 1.15 (t, 3H, CH$_3$CH$_2$, J=7.1 Hz), 1.20 (t, 3H, CH$_3$CH$_2$, J=7.1 Hz), 2.63 (s, 3H, CH3), 4.03 (q, 2H, CH$_2$CH$_3$, J=7.1 Hz), 4.13 (s, 2H, CH$_2$Ph), 4.17 (q, 2H, CH$_2$CH$_3$, J=7.1 Hz), 4.78 (s, 2H, OCH$_2$), 4.90 (s, 2H, OCH$_2$), 6.41 (d, 1H, J=2.2 Hz), 6.44 (d, 1H, J=2.2 Hz), 7.13–7.33 (m, 10H, Ph).

Example 23

Preparation of 5,7-Bis(hydroxyaminocarbonylmethoxy)-1,3-dibenzyl-4-methyl-2(1H)-quinolinone

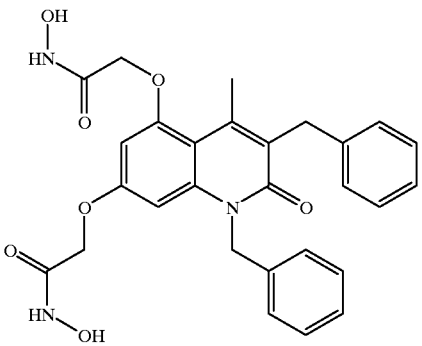

The product from the previous example (0.3 g), hydroxylamine hydrochloride (0.32 g) and 5 N NaOH (1.05 ml) were reacted in ethanol (8 ml) at 50° C. for six hours. The reaction mixture was treated with water and made basic (pH 10) and filtered. The filtrate was acidified to pH 2 and filtered. Yield: 0.2 g, melting point 121–127° C.

$^1$H-NMR (400 MHz, DMSO-$d_6$): the tautomeric forms of hydroxamic acid are seen in OCH$_2$-signals: 2.63 (s,3H, CH3), 4.13 (S, 2H, CH$_2$Ph), 4.41 (s, 2H, OCH$_2$), 4.54 (s, 2H,OCH$_2$), 4.64 (s, 2H, HON=C(OH)CH$_2$O), 4.65 (s, 2H, HON=C(OH)CH$_2$O), 4.77 (s, 2H, HON=C(OH)CH$_2$O), 4.78 ((s, 2H, HON=C(OH)CH$_2$O), 5.54 (s, 2H, NCH$_2$Ph), 6.38–6.54 (m, 2H, ArH), 7.14–7.34 (m, 10 H, Ph), 9.05 (b, 2H, NOH), 10.84 (s, 1H, HONHCO), 10.88 (s, 1H, HONHCO).

Example 24

Preparation of 5,7-Bis -[1-(6-hydroxypyridazinyl)]oxy-1,3-dibenzyl-4-methyl-2(1H)-quinolinone a) 5,7-Bis-[1-(6-chloropyridazinyl)]oxy-1,3-dibenzyl-4-methyl-2(1H)-quinolinone

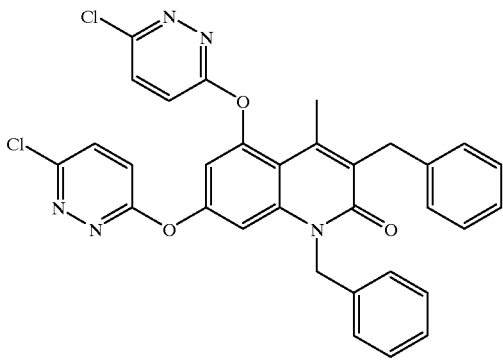

A mixture of 1,3-dibenzyl-5,7-dihydroxy-4-methyl-2(1H)-quinolinone (0.5 g), 3,6-dichloropyridazine (0.83 g) and potassium carbonate (0.75 g) in DMF (12,5 ml) was stirred at 80° C. for 4 hours. The reaction mixture was treated with water at pH 8 and filtered. The solids were recrystallized from ethanol-DMF (2:1). Yield 0.5 g. Melting point 208–218° C.

$^1$H-NMR (DMSO-d$_6$, 300 MHz): 2.43 (s, 3H,CH$_3$), 4.16 (s, 2H, CH$_2$Ph), 5.58 (s, 2H, NCH$_2$Ph), 7.09–7.33 (m, 12H, ArH+Ph), 7.55 (d, 1H, PyridH, J=9,2 Hz), 7.70 (d, 1H, PyridH, J=9,2 Hz),7.93 (d, 1H, PyridH, J=9,2 Hz), 7.98 (d, 1H, PyridH, J=9,2 Hz).

b) 5,7-Bis -[1-(6-hydroxypyridazinyl)]oxy-1,3-dibenzyl-4-methyl-2(1H)-quinolinone

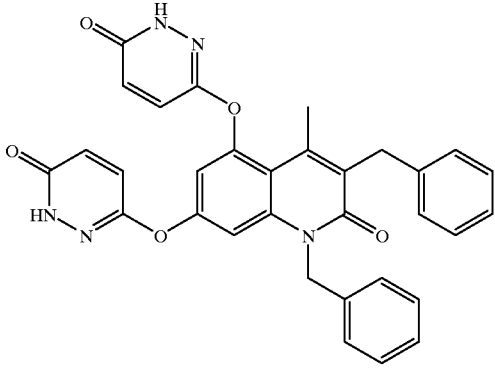

The product from the previous example (0.2 g) and potassium acetate (0.13 g) in acetic acid (5 ml) were refluxed for 4 hours. The mixture was evaporated, treated with water at pH 10 and filtered. The filtrate was acidified to pH 6 and filtered. Yield 70 mg.

$^1$H-NMR (DMSO-d6, 300 MHz): 2.47 (s, 3H, CH$_3$), 4.15 (s, 2H, CH$_2$Ph), 5.55 (s, 2H, NCH$_2$), 6.93–7.34 (m, 15 H, PyridH+ArH+Ph), 7.47 (d, 1H, J=10 Hz), 12.25 (s, 1H, NH), 12.38 (s, 1H NH).

What is claimed is:

1. A method for obtaining direct dilatation of the coronary arteries comprising administering to a mammal in need thereof a therapeutically effective amount of a phospholamban inhibitor.

2. A method for the treatment of coronary heart disease comprising administering to a mammal in need thereof a therapeutically effective amount of a phospholamban inhibitor.

3. A method for the treatment of hemodynamic crisis in which the low aortic blood pressure decreases coronary perfusion pressure comprising administering to a mammal in need thereof a therapeutically effective amount of a phospholamban inhibitor.

4. A compound of formula (I) or (II):

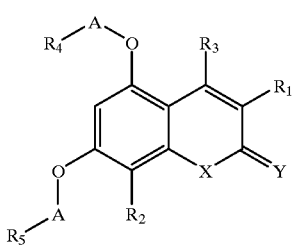

(I)

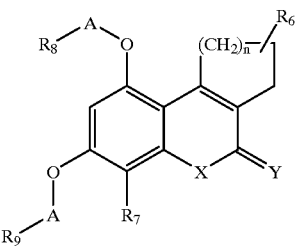

(II)

wherein:

R$_1$ is hydrogen, alkyl, alkenyl, aryl, arylalkyl, hydroxyalkyl, halogenalkyl, alkoxy, COR$_{10}$, CONR$_{10}$R$_{11}$, OR$_{10}$, S(O)$_m$R$_{10}$, NR$_{10}$COR$_{11}$, or NR$_{10}$R$_{11}$, where R$_{10}$ is hydrogen, alkyl, alkenyl, aryl, arylalkyl, hydroxyalkyl, halogenalkyl, alkoxy or hydroxy and R$_{11}$ is hydrogen, alkyl, aryl, arylalkyl, alkoxy, aryloxy, hydroxy or acyl, or when X is NR$_{11}$, R$_1$ is also carboxylalkyl;

R$_6$ is hydrogen, alkyl, alkenyl, aryl, or arylalkyl;

R$_2$ and R$_7$ are hydrogen, alkyl, aryl, arylalkyl, alkenyl, COR$_{10}$, CONR$_{10}$R$_{11}$, halogen, trifluoromethyl, nitro or cyano, where R$_{10}$ and R$_{11}$ are as defined above;

R$_3$ is hydrogen, alkyl, aryl or arylalkyl;

A is alkyl or substituted alkyl;

m is 0–2 and n is 1–3;

Y is O, NR$_{11}$ or S, where R$_{11}$ is as defined above;

X is O, NR$_{11}$ or S, where R$_{11}$ is as defined above;

R$_4$, R$_5$, R$_8$ and R$_9$ are independently one of the following groups:

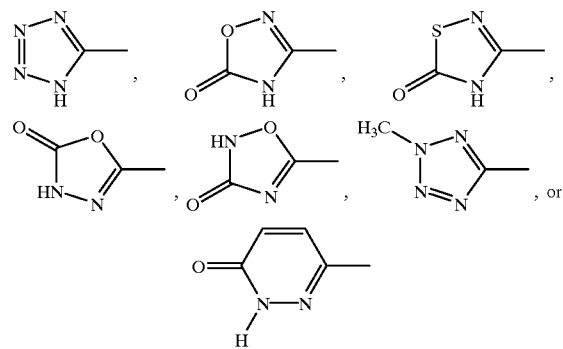

or where X is NR$_{11}$, R$_4$, R$_5$, R$_8$ and R$_9$ are also independently HOOC—, R$_{12}$OOC—, H$_2$NCO— or HOHNCO—, wherein R$_{12}$ is alkyl, arylalkyl or aryl, and wherein each aryl residue defined above by itself or as part of another group is optionally substituted;

and pharmaceutically acceptable salts and esters thereof.

5. A compound of claim 4 wherein said compound has formula (I) and R$_2$ is hydrogen.

6. A compound of claim 5 wherein R$_1$ is hydrogen, C$_{1-6}$ alkyl, C$_{2-6}$ alkenyl, C$_{6-10}$ aryl, C$_{7-12}$ arylalkyl, C$_{1-6}$ hydroxyalkyl, C$_{1-6}$ halogenalkyl or C$_{1-6}$ alkoxy.

7. A compound of claim 6 wherein Y is O or S, and X is O.

8. A compound of claim 6 wherein Y is O or S; and X is NR$_{11}$, where R$_{11}$ is hydrogen, C$_{1-6}$ alkyl, C$_{6-10}$ aryl, C$_{7-12}$ arylalkyl, C$_{1-6}$ alkoxy, C$_{6-10}$ aryloxy, hydroxy, C$_{1-6}$ alkanoyl or C$_{1-6}$ carboxyalkyl.

9. A compound of claim 8, wherein $R_3$ is hydrogen, $C_{1-6}$ alkyl, $C_{6-10}$ aryl, or $C_{7-12}$ arylalkyl.

10. A compound of claim 9, wherein $R_3$ is $C_{1-6}$ alkyl.

11. A compound of claim 10, wherein A is straight-chain or branched $C_{1-4}$ alkylene and $R_4$ and $R_5$ are independently

[structures shown]

or where X is $NR_{11}$, $R_4$ and $R_5$ are also HOOC—, $R_{12}$OOC—, $H_2$NCO— or HOHNCO—, where $R_{12}$ is $C_{1-6}$ alkyl, $C_{6-10}$ aryl, or $C_{7-12}$ arylalkyl.

12. A compound of claim 4, wherein said compound has formula (II) and $R_7$ is hydrogen.

13. A compound of claim 12, wherein $R_6$ is hydrogen, $C_{1-6}$ alkyl, $C_{6-10}$ aryl, or $C_{7-12}$ arylalkyl; and n is 1, 2 or 3.

14. A compound of claim 13, wherein Y is O or S, and X is O.

15. A compound of claim 13, wherein Y is O or S; and X is $NR_{11}$, where $R_{11}$ is hydrogen, $C_{1-6}$ alkyl, $C_{6-10}$ aryl, $C_{7-12}$ arylalkyl, $C_{1-6}$ alkoxy, $C_{6-10}$ aryloxy, hydroxy, $C_{1-6}$ alkanoyl or $C_{1-6}$ carboxyalkyl.

16. A compound of claim 14, wherein A is straight-chain or branched $C_{1-4}$ alkylene.

17. A compound of claim 16, wherein $R_4$ and $R_5$ are independently

[structures shown]

or where X is $NR_{11}$, $R_4$ and $R_5$ are also HOOC—, $R_{12}$OOC—, $H_2$NCO— or HOHNCO—, where $R_{12}$ is $C_{1-6}$ alkyl, $C_{6-10}$ aryl, or $C_{7-12}$ arylalkyl.

18. A pharmaceutical composition comprising a compound of claim 4 as an active ingredient together with pharmaceutically acceptable carrier.

19. A method of treating heart failure comprising administering to a subject in need thereof a therapeutically effective amount of a compound of claim 4.

20. A method for the treatment and prevention of stunned myocardium comprising administering to a subject in need thereof a therapeutically effective amount of a compound of claim 4.

21. A compound of formula (XXV):

(XXV)

[structure]

wherein $R_1$ is hydrogen, alkyl, alkenyl, aryl, arylalkyl, hydroxyalkyl, halogenalkyl, alkoxy, $COR_{10}$, $CONR_{10}R_{11}$, $OR_{10}$, $S(O)_mR_{10}$, $NR_{10}COR_{11}$ or $NR_{10}R_{11}$, where $R_{10}$ is hydrogen, alkyl alkenyl, aryl, arylalkyl, hydroxyalkyl, halogenalkyl, alkoxy or hydroxy and $R_{11}$ is hydrogen, alkyl, aryl, arylalkyl, alkoxy, aryloxy, hydroxy or acyl, or carboxylalkyl;

$R_3$ is hydrogen, alkyl, aryl or arylalkyl;

m is 0–2;

$R_{11}$ is hydrogen, alkyl, aryl, arylalkyl, alkoxy, aryloxy, hydroxy or acyl, or carboxylalkyl, and wherein each aryl residue defined above by itself or as part of another group is optionally substituted.

22. A method for obtaining direct dilatation of the coronary arteries comprising administering to a mammal in need thereof a therapeutically effective amount of a compound of claim 4.

23. A method for the treatment of coronary heart disease comprising administering to a mammal in need thereof a therapeutically effective amount of a compound of claim 4.

24. A method for the treatment of hemodynamic crisis in which the low aortic blood pressure decreases coronary perfusion pressure comprising administering to a mammal in need thereof a therapeutically effective amount of a compound of claim 4.

25. A compound of claim 4, which is selected from the group consisting of:

3-benzyl-5,7-bis[(1H-tetrazol-5-yl)methoxy]-4-methyl-2H-1-benzopyran-2-one;
7,8,9,10-tetrahydro-1,3-bis[(1H-tetrazol-5-yl)methoxy]-7-phenyl-6H-dibenzo[b,d]pyran-6-one;
3-benzyl-5,7-bis[(2,5-dihydro-5-oxo-4H-1,2,4-oxadiazol-3-yl)-methoxy]-4-methyl-2H-1-benzopyran-2-one,
7,8,9,10-tetrahydro-bis[(1H-tetrazol-5-yl)methoxy]-1,3-dihydroxy-6H-dibenzo[b,d]pyran-6-one;
5,7-bis[(1H-tetrazol-5-yl)methoxy]-4-phenyl-2H-1-benzopyran-2-one;
7,8,9,10-tetrahydro-1,3-bis[(1H-tetrazol-5-yl)methoxy]-8-phenyl-6H-dibenzo[b,d]pyran-6-one;
5,7-bis[(1H-tetrazol-5-yl)methoxy]-4-methyl-3-(2-phenylethyl)-2H-1benzopyran-2-one;
5,7-bis[(1H-tetrazol-5-yl)methoxy]-1,3-dibenzyl-4-methyl-2(1H)-quinolinone;
5,7-bis[(1H-tetrazol-5-yl)methoxy]-3-benzyl-1,4-dimethyl-2(1H)-quinolinone;
3-benzyl-5,7-bis[(2-methyl-1H-tetrazol-5-yl)methoxy]-4-methyl-2H-1-benzopyran-2-one;
3-benzyl-5,7-bis[(1-(1H-tetrazol-5-yl)ethoxy]4-methyl-2H-1-benzopyran-2-one;
5,7-bis(carboxymethoxy)-1,3-dibenzyl-4-methyl-2(1H)-quinolinone;
3-benzyl-5,7-bis[(1H-tetrazol-5-yl)methoxy]-1-(4-fluorobenzyl)-4-methyl-2(1H)-quinolinone;

5,7-bis[(1H-tetrazol-5-yl)methoxy]-3-(4-chlorobenzyl)-4-methyl-2H-1-benzopyran-2-one;

5,7-bis[(1H-tetrazol-5-yl)methoxy]- 3-(4-nitrobenzyl)-4-methyl-2H-1-benzopyran-2-one;

5,7-bis[(1H-tetrazol-5-yl)methoxy]-3-cyclopentyl-4-methyl-2H-1-benzopyran-2-one;

5,7-bis[(1H-tetrazol-5-yl)methoxy]-4-methyl-3-(1-naphthylmethyl)-2H-1-benzopyran-2-one;

1-benzyl-5,7-bis[(1H-tetrazol-5-yl)methoxy]-4-methyl-2(1H)-quinolinone, 1-benzyl-5,7-bis[(1H-tetrazol-5-yl)methoxy]-3-(2-fluorobenzyl)-4-methyl-2(1H)-quinolinone;

1-benzyl-5,7-bis[(1H-tetrazol-5-yl)methoxy]-4-methyl-3-(2-phenylethyl)-2(1H)-quinolinone;

5,7-bis(aminocarbonylmethoxy)-1,3-dibenzyl-4-methyl-2(1H)-quinolinone;

5,7-bis(ethoxycarbonylmethoxy)-1,3-dibenzyl-4-methyl-2(1H)-quinolinone, 5,7-bis(hydroxyaminocarbonylmethoxy)-1,3-dibenzyl-4-methyl-2(1H)-quinolinone; and 5,7-bis[1-(6-hydroxypyridazinyl)]oxy-1,3-dibenzyl-4-methyl-2(1H)-quinolinone.

26. A compound of claim 4, wherein said compound is 5,7-bis[(1H-tetrazol-5-yl)methoxyl]-1,3-dibenzyl-4-methyl-2(1H)-quinolinone.

27. A compound of claim 4, wherein Y is O.

28. A compound of claim 4, wherein X is O.

29. A compound of claim 4, wherein X is $NR_{11}$, and $R_{11}$ is hydrogen, $C_{1-4}$ alkyl or $C_{6-10}$ aryl($C_{1-6}$)alkyl.

30. A compound of claim 4, wherein said compound has formula (I) and $R_3$ is $C_{1-4}$ alkyl.

31. A compound of claim 4, wherein $R_1$ is benzyl or phenethyl.

32. A compound of claim 4, wherein said compound has formula (I) and $R_4$ and $R_5$ are each

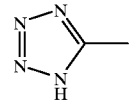

33. A compound of claim 4, wherein said compound has formula (II) and $R_8$ and $R_9$ are each

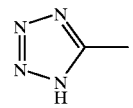

* * * * *